US007141383B2

(12) United States Patent
Kostenis et al.

(10) Patent No.: US 7,141,383 B2
(45) Date of Patent: Nov. 28, 2006

(54) EDG8 RECEPTOR, ITS PREPARATION AND USE

(75) Inventors: Evi Kostenis, Frankfurt am Main (DE); Johann Gassenhuber, Wiesbaden (DE)

(73) Assignee: Sanofi-Aventis Deutschland GmbH, Frankfurt (DE)

(*) Notice: Subject to any disclaimer, the term of this patent is extended or adjusted under 35 U.S.C. 154(b) by 0 days.

(21) Appl. No.: 10/421,828

(22) Filed: Apr. 24, 2003

(65) Prior Publication Data

US 2003/0219874 A1 Nov. 27, 2003

Related U.S. Application Data

(62) Division of application No. 09/842,316, filed on Apr. 26, 2001, now abandoned.

(30) Foreign Application Priority Data

Apr. 26, 2000 (EP) .................................. 1088582
Aug. 1, 2000 (EP) .................................. 1165893

(51) Int. Cl.
*G01N 33/567* (2006.01)
(52) U.S. Cl. ...................... 435/7.2; 435/7.21
(58) Field of Classification Search ............... 435/7.21, 435/501
See application file for complete search history.

(56) References Cited

FOREIGN PATENT DOCUMENTS

| EP | 1 090 925 A1 | 4/2001 |
| WO | WO 99/19513 | 4/1999 |
| WO | WO 00/11166 | 3/2000 |
| WO | WO 0011166 * | 3/2000 |
| WO | WO 00/22129 | 4/2000 |
| WO | WO 01/04139 A2 | 1/2001 |

OTHER PUBLICATIONS

Hla et al, "Sphingosine-1-Phosphate Signaling via the EDG-1 Family of G-Protein-Coupled Receptors", Annals New York Academry of Sciences, pp. 16-24.
Im et al., "Characterization of a Novel Sphingosine 1-Phosphate Receptor, Edg-8", The Journal of Biological Chemistry, May 12, 2000, vol. 275, No. 19, pp. 14281-14286.
Glickman et al., Molecular Cloning, Tissue-Specific Expression, and Chromosomal Localization of a Novel Nerve Growth Factor-Regulated G-Protein-Coupled Receptor, nrg-1, Molecular and Cellular Neuroscience 14, pp. 141-152, 1999.
An et al., "Signaling Mechanism and Molecular Chahracteristics of G Protein-Coupled Receptors for Lysophosphatidic Acid and Sphingosine 1-Phosphate", Journal of Cellular Biochemistry Supplements, 30/31, pp. 147-157, 1998.
Im et al., "Homo sapiens sphingosine 1-phosphate receptor Edg-8 gene, complete cds", Database EM_HUM Online, 1 p., Dec. 6, 2000.
Ebi, Homo sapiens chromosome 19 clone CTC-429L19, Working Draft Sequence, 4 Ordered Pieces, 13 pgs. Oct. 8, 1999.

An et al.; Characterization of a Novel Subtype of Human G Protein-coupled Receptor for Lysophosphatidic Acid; The Journal of Biological Chemistry; vol. 273, No. 14, Issue of Apr. 3, pp. 7906-7910, 1998.
An et al.; Sphingosine 1-Phosphateinduced Cell Proliferation, Survival, and Related Signaling Events Mediated by G Protein-coupled Receptors Edg3 and Edg5;; The Journal of Biological Chemistry; vol. 275, No. 1, Issue of Jan. 7, pp. 288-296, 2000.
An et al., Transduction Of Intracellular Calcium Signals through G Protein-Mediated Activation of Phospholipase C by Recombinant Sphingosine 1-Phosphate Receptors; The American Society for Pharmacology and Experimental Therapeutics; pp 787-794; (1999).
Ancellin et al., Differential Pharmacological Properties and Signal Transduction of the Sphingosine 1-Phosphate Receptors EDG-1, EDG-3, and EDG-5 vol. 274, No. 27, Issue of Jul. 2, pp. 18997-19002, (1999).
Okano et al., Myelin Basic Protein Gene and the Function of Antisense RNA in Its Repression in Myelin-Deficient Mutant Mouse; Journal of Neurochemistry; vol. 56, No. 2, 1999 pp. 560-567.
Barbas III et al., Combinatorial Immunoglobulin Libraries on the Surface of Phage (Phabs): Rapid Selection of Antigen-Specific Fabs; Methods A Companion to Methods in Enzymology, vol. 2, No. 2, Apr. pp. 119-124, (1991).
Bitter et al., Expression and Secretion Vectors for Yeast; Methods in Enzymology, vol. 153, pp. 516-544.
Bunemann et al., A Novel Membrane Receptor with High Affinity for Lysosphingomyelin and Sphingosine 1-phosphate in Atrial Myocytes; The EMB Journal vol. 15. No. 20 pp. 5527-5534, 1996.
Carter et al./ Humanization of an Anti-p185 . . . ; Proc. Natl. Acad. Sci USA; vol. 89, pp. 4285-4289, May 1992.
Chao et al.; Sphingosine-mediated Phosphatidylinositol . . . The Journal of Biological Chemistry, vol. 269, No. 8, Feb. 25, 1994; pp. 5849-5856.
Cooney et al.; Site Specific Oligonucleotide Binding . . . Science, vol. 241; pp. 456-459.
Corpet, Muliple Sequence Alignment . . . ; Nucleic Acids Research; vol. 16, 1988; pp. 10881-10890.
Cotton; Reactivity of Cytosine . . . ; Proc Natl. Acad. Sci., vol. 85, pp. 4397-4401; Jun. 1988.
Dervan et al., Second Structural Motif . . . ; Science, vol. 251; pp. 13601363; 1991.
Duriex et al./ Responses to Spingosine-1 . . . ; Amer. Physic. Society; pp. 1360-1364 (May 1993) 2641 (5 p21).
Ghosh et al., Sphingosine 1-Phosphate . . . ; Journal of Biological Chemistry; vol. 269, No. 36, Sep. 1994; pp. 22628-22635.
Glickman et al.; Molecular Cloning . . . ; Molecular and Cellular Neuroscience 14, pp. 141-152 (1999).
Gohla et al.; Differential Involvement of . . . ; The Hournal of Biological Chemistry; vol. 274, No. 25, Jun. 18, 1999; pp. 17901-17907.

(Continued)

*Primary Examiner*—John Ulm

(57) ABSTRACT

The present invention relates to newly identified human EDG8 receptors, polynucleotides encoding this receptor, polypeptides encoded by such polynucleotides, the preparation and the use of such polynucleotides and polypeptides.

6 Claims, 24 Drawing Sheets

OTHER PUBLICATIONS

Gonda; The Novel Sphingosine . . . ; Biochem J. (1999) 337, 67-75.
Green et al., Antigen-Specific Human Monoclonal . . . ; Nature Genetics, vol. 7, May 1994; pp. 13-21.
Gueguen et al.; Structure—Activity Analysis . . . ; Biochemistry 199, 38, 8440-8450.
Hisano et al., Induction and Suppression . . . ; Blood, vol. 93, No. 12; Jun. 15, 1999; pp. 4293-4299.
Nordstrom et al.; Translational Control By Antisense . . . ; Gene, 72 (1988) 237-240.
Higgins et al., Fast and Sensitive Multiple . . . ; Cabios Communications; vol. 5, No. 2, 1989 pp. 151-153.
Hla et al., Sphingosine-1 . . . ; Biochemical Pharm; vol. 58, pp. 201-207; 1999.
Hla et al.; An Abundant Transcript . . . ; Journal of Biological Chemistry; vol. 265, No. 16; 1990; pp. 9308-9313.
Huang et al., Parallelization of Local . . . ; Cabios; vol. 8, No. 2, pp. 155-165.
Im et al., Molecular Clonging and . . . , Computer Applications in the Biosciences; 8:1-06 (1992).
Jalink et al.; Lysophosphatidic Acid . . . , Biochem Biophys. Acta 1198:185 (1994).
Jalink et al., Biochem Biophysica Acta; 1198 (1994) 185-196.
Jones et al., Replacing the Complementarity . . . , Nature vol. 321; May 1986; pp. 522-525.
Kon et al., Journal of Biological Chemistry; vol. 274, No. 34, Aug. 1999; pp. 23940-23947.
Kohler et al.,; Continuous Cultures . . . , Nature vol. 256, Aug. 1975; pp. 495-497.
Kostenis et al., The N-Terminal Extension; The Journal of Biological Chemistry; vol. 272, No. 31, 1997; pp. 19107-1911.
Lee et al., Complexes Formed By . . . ; Nucleic Acids Research; vol. 6, No. 9; 1979; pp. 3073-3091.
Lee et al., The Inducible G Protein . . . ; Journal of Biological, vol. 271, No. 19; May 1996; pp. 11272-11279.
Lee et al., Sphingosine-1-Phosphate . . . ; Science, vol. 279; Mar. 1998; pp. 1552-1555.
Lee et al., Lysophosphatidic Acid . . . ; Journal of Biological Chemistry; vol. 273, No. 34, Aug. 1998, pp. 22105-22112.
Lee et al., Vascular Endothelial . . . , Cell, vol. 99, 301-312, Oct. 1999.
Lonberg et al., Antigen-Specific Human . . . , Nature, vol. 368, Apr. 1994, pp. 856-859.
Losman et al., Baboon Anti-Idiotype Antibodies . . . , Int. J. Cancer, 46, pp. 310-314, 1990.
Lynch et al., Life On The edg . . . , Elsevier Science Ltd., 1999, vol. 20; pp. 473-475.
Mattie et al., Sphingosine-1-Phosphate . . . , Journal of Biological Chemistry; vol. 269, No. 5, Feb. 1994; pp. 3181-3188.
Heringdorf et al., Calcium Signalling . . . ; Naunyn-Schmiedeberg's Arch Pharmacol (1996) pp. 397-403.
Moolenaar et al., Lysophosphatidic Acid . . . ; Current Opinion in Cell Biol 9: pp. 168-173 (1997).
Morris; One Wheel On My Wagon . . . ; Trends Pharmacol Science 20; pp. 393-395, (1999).

Myers et al., Detection of Single Base . . . ; Science, vol. 230; pp. 12421246, (1985).
Needleman et al., A General Method Applicable . . . ; J. Mol Biol. (1970) 48, pp. 443-353.
Noh et al., Different Signaling Pathway . . . ; Journal of Cellular Physiology 176; (1999) pp. 412-423.
Okajima et al., Involvement of Pertussis . . . ; J. Biol Chem 273; (1998) pp. 260-264.
Okamoto et al., EDG1 Is a Functional . . . ; Journal of Biological Chemistry; vol. 273, No. 42, pp. 271041-27110, (1998).
Orlandi et al., Cloning Immunoglobulin . . . ; Proc. Natl. Acad. Scie, vol. 86, pp. 3833-3837, May 1989.
Pearson; Using the FASTA Program . . . ; Methods in Molecular Biology 24; pp. 306-331 (1994).
Pearson et al., Improved Tools for . . . ; Proc. Natl. Acad. Sci., vol. 85, pp. 2444-2448, Apr. 1988.
Postma et al., Sphingosine-1- . . . ; The EMBO Journal; vol. 15 No. 10 pp. 2388-2395, 1996.
Pyne et al., Sphingosine 1-phosphate; Biochem J. (2000) 349, 385-402.
Sadahira et al., Sphingosine 1-phosphate . . . ; Proc. Natl. Acad. Sci. vol. 89, pp. 9686-9690, Oct. 1992.
Rizza et al., Lysophosphatidic Acid . . . ; Laboratory Investigation, vol. 79, No. 10, pp. 1227-1233, 1999.
Saiki et al., Analysis of Enzymatically . . . ; Nature vol. 324, 1986, pp. 163-166.
Schulze et al., Lysophosphatidic Acid Increases . . . ; Journal of Neurochemistry; vol. 68, No. 3, 1997, pp. 992-1000.
Siess et al., Lysophosphatidic Acid . . . Proc. Natl. Acad. Sci., vol. 96, pp. 6931-6936, 1999.
Smith et al., Comparison of Biosequences; Advances in Applied Mathematics 2, pp. 482-489; (1981).
Tokumura et al., Stimulatory Effect of . . . ; Arch. Int. Pharmacodyn. 245, pp. 74-83 (1980).
Tokumura et al., Vasopressor Effect of . . . ; Research Communications in Molecular Pathology and Pharmacology; vol. 90, No. 1, Oct. 1995.
Tornquist et al., Sphingosine 1-Phosphate . . . ; Endocrinology, vol. 138, No. 10, pp. 4049-4057, 1997.
Van Brocklyn et al., Sphingosine-1-phosphate . . . ; Blood, vol. 95, No. 8, (Apr. 2000).
van Koppen et al., Activation of High Affinity: The Journal of Biological Chemistry; vol. 271, No. 4, pp. 2082-2087, 1996.
Xia et al., Activiation of Sphingosine Kinase . . . ; The Journal of Biological Chemistry; vol. 274, No. 48, Nov. 1999; pp. 34499-34505.
Yamazaki et al., Egg-6 as a Putative . . . Biochemical and Biophysical Research Communications 268, pp. 583-589 (2000).
Yatomi et al., Sphingosine 1-Phosphate . . . ; Biochem, 121, pp. 969-973 (1997).
Yatomi et al., Sphingosine 1-Phosphate . . . ; Biochem, vol. 272, No. 8, pp. 5291-5297, 1997.

* cited by examiner

FIG. 1A

```
  1 ATGGAGTCGGGGCTGCTGCGGCCGGCGCCGGTGAGCGAGGTCATCGTCCTGCATTACAAC
    M   E   S   G   L   L   R   P   A   P   V   S   E   V   I   V   L   H   Y   N

61 TACACCGGCAAGCTCCGCGGTGCGCGCTACCAGCCGGGTGCCGGCCTGCGCGCCGACGCC
    Y   T   G   K   L   R   G   A   R   Y   Q   P   G   A   G   L   R   A   D   A

121 GTGGTGTGCCTGGCGGTGTGCGCCTTCATCGTGCTAGAGAATCTAGCCGTGTTGTTGGTG
    V   V   C   L   A   V   C   A   F   I   V   L   E   N   L   A   V   L   L   V

181 CTCGGACGCCACCCGCGCTTCCACGCTCCCATGTTCCTGCTCCTGGGCAGCCTCACGTTG
    L   G   R   H   P   R   F   H   A   P   M   F   L   L   L   G   S   L   T   L

241 TCGGATCTGCTGGCAGGCGCCGCCTACGCCGCCAACATCCTACTGTCGGGGCCGCTCACG
    S   D   L   L   A   G   A   A   Y   A   A   N   I   L   L   S   G   P   L   T

301 CTGAAACTGTCCCCCGCGCTCTGGTTCGCACGGGAGGGAGGCGTCTTCGTGGCACTCACT
    L   K   L   S   P   A   L   W   F   A   R   E   G   G   V   F   V   A   L   T

361 GCGTCCGTGCTGAGCCTCCTGGCCATCGCGCTGGAGCGCAGCCTCACCATGGCGCGCAGG
    A   S   V   L   S   L   L   A   I   A   L   E   R   S   L   T   M   A   R   R

421 GGGCCCGCGCCCGTCTCCAGTCGGGGGCGCACGCTGGCGATGGCAGCCGCGGCCTGGGGC
    G   P   A   P   V   S   S   R   G   R   T   L   A   M   A   A   A   A   W   G

481 GTGTCGCTGCTCCTCGGGCTCCTGCCAGCGCTGGGCTGGAATTGCCTGGGTCGCCTGGAC
    V   S   L   L   L   G   L   L   P   A   L   G   W   N   C   L   G   R   L   D

541 GCTTGCTCCACTGTCTTGCCGCTCTACGCCAAGGCCTACGTGCTCTTCTGCGTGCTCGCC
    A   C   S   T   V   L   P   L   Y   A   K   A   Y   V   L   F   C   V   L   A
```

FIG. 1B

```
 601 TTCGTGGGCATCCTGGCCGCTATCTGTGCACTCTACGCGCGCATCTACTGCCAGGTACGC
      F  V  G  I  L  A  A  I  C  A  L  Y  A  R  I  Y  C  Q  V  R

661 GCCAACGCGCGGCGCCTGCCGGCACGGCCCGGGACTGCGGGGACCACCTCGACCCGGGCG
      A  N  A  R  R  L  P  A  R  P  G  T  A  G  T  T  S  T  R  A

721 CGTCGCAAGCCGCGCTCGCTGGCCTTGCTGCGCACGCTCAGCGTGGTGCTCCTGGCCTTT
      R  R  K  P  R  S  L  A  L  L  R  T  L  S  V  V  L  L  A  F

781 GTGGCATGTTGGGGCCCCCTCTTCCTGCTGCTGTTGCTCGACGTGGCGTGCCCGGCGCGC
      V  A  C  W  G  P  L  F  L  L  L  L  D  V  A  C  P  A  R

841 ACCTGTCCTGTACTCCTGCAGGCCGATCCCTTCCTGGGACTGGCCATGGCCAACTCACTT
      T  C  P  V  L  L  Q  A  D  P  F  L  G  L  A  M  A  N  S  L

901 CTGAACCCCATCATCTACACGCTCACCAACCGCGACCTGCGCCACGCGCTCCTGCGCCTG
      L  N  P  I  I  Y  T  L  T  N  R  D  L  R  H  A  L  L  R  L

961 GTCTGCTGCGGACGCCACTCCTGCGGCAGAGACCCGAGTGGCTCCCAGCAGTCGGCGAGC
      V  C  C  G  R  H  S  C  G  R  D  P  S  G  S  Q  Q  S  A  S

1021 GCGGCTGAGGCTTCCGGGGGCCTGCGCCGCTGCCTGCCCCCGGGCCTTGATGGGAGCTTC
      A  A  E  A  S  G  G  L  R  R  C  L  P  P  G  L  D  G  S  F

1081 AGCGGCTCGGAGCGCTCATCGCCCCAGCGCGACGGGCTGGACACCAGCGGCTCCACAGGC
      S  G  S  E  R  S  S  P  Q  R  D  G  L  D  T  S  G  S  T  G
1141 AGCCCCGGTGCACCCACAGCCGCCCGGACTCTGGTATCAGAACCGGCTGCAGACTGA
      S  P  G  A  P  T  A  A  R  T  L  V  S  E  P  A  A  D  *
```

FIG. 1D

```
                1                                                                    60
edg2_human   MAAISTSIPV ISQPQETAMN EPQCFYNESI AFFYNRSGKH LAT.EWNTVS KLVMGL..GI
edg7_human   ---------- -------MN E..CHYDKHM DFFYNRSNTD TVD.DW.TGT KLVIVLCVGT
edg4_human   ---------- -------MVI MGQCYYNETI GFFYNNSGKE LSS.HWR..P KDVVVVALGL
edg1_human   -----MGPTS VPLVKAHRSS VSDYVNYDII VRHYNYTGKL ..NISADKEN SIKLTSVVFI
edg3_human   ---------- --MATALPPR LQPVRGNETL REHYQYVGKL AGRLKEASEG S.TLTTVLFL
edg5_human   ---------- ------MGSL YSEYLNPNKV QEHYNYTKE. ...TLETQETT SRQVASAFIV
edg8_human   ---------- -----MESGL LRPAPVSEVI VLHYNYTGKL RG.ARYQPGA GLRADAVVCL
edg6_human   -----MNATG TPVAPESCQQ LAAGGHSRLI VLHYNHSGRL AGR.GGPEDG GLGALRGLSV 61                                                                   120
edg2_human   TVCIFIMLAN LLVMVAIYVN RRFHFPIYYL MANLAAADFF AGLAYFYLMF MTGPNTRRLT
edg7_human   FFCLFIFFSN SLVIAAVIKN RKFHFPFYYL LANLAAADFF AGIAYVFLMF NTGPVSKTLT
edg4_human   TVSVLVLLTN LLVIAAIASN RRFHQPIYYL LGNLAAADLF AGVAYLFLMF HTGPRTARLS
edg1_human   LICCFIILEN IFVLLTIWKT KKFHPPMYYF IGNLALSDLL AGVAYTANLL LSGATTYKLT
edg3_human   VICSFIVLEN LMVLIAIWKN NKFHRRMYFF IGNLALCDLL AGIAYKVNIL MSGKKTFSLS
edg5_human   ILCCAIVVEN LLVLIAVARN SKFHSAMYLF LGNLAASDLL AGVAFVANTL LSGSVTLRLT
edg8_human   AVCAFIVLEN LAVLLVLGRH PRFHAPMFLL LGSLTLSDLL AGAAYAANIL LSGPLTLKLS
edg6_human   AASCLVVLEN LLVLAAITSH MRSRRWVYYC LVNITLSDLL TGAAYLANVL LSGARTFRLA 121                                                                  180
edg2_human   VSTWLLRQGL IDTSLTASVA NLLAIAIERH ITVFR.MQLH TRMSNRRVVV VIVVIWTMAI
edg7_human   VNRWFLRQGL LDSSLTASLT NLLVIAVERH MSIMR.MRVH SNLTKKRVTL LILLVWAIAI
edg4_human   LEGWFLRQGL LDTSLTASVA TLLAIAVERH RSVMA.VQLH SRLPRGRVVM LIVGVWVAAI
edg1_human   PAQWFLREGS MFVALSASVF SLLAIAIERY ITMLK.MKLH NGSNNFRLFL LISACWVISL
edg3_human   PTVWFLREGS MFVALGASTC SLLAIAIERH LTMIK.MRPY DANKRHRVFL LIGMCWLIAF
edg5_human   PVQWFAREGS ASITLSASVF SLLAIAIERH VAIAK.VKLY GSDKSCRMLL LIGASWLISL
edg8_human   PALWFAREGG VFVALTASVL SLLAIALERS LTMAR.RGPA PVSSRGRTLA MAAAAWGVSL
edg6_human   PAQWFLREGL LFTALAASTF SLLFTAGERF ATMVRPVAES GATKTSPVYG FIGLCWLLAA 181                                                                  240
edg2_human   VMGAIPSVGW NCICDIENCS NMAPLYSDSY LVFWAIFNLV TFVVMVVLYA HIFGYVRQRT
edg7_human   FMGAVPTLGW NCLCNISACS SLAPIYSRSY LVFWTVSNLM AFLIMVVVYL RIYVYVKRKT
edg4_human   GLGLLPAHSW HCLCALDRCS RMAPLLSRSY LAVWALSSLL VFLLMVAVYT RIFFYVRRRV
edg1_human   ILGGLPIMGW NCISALSSCS TVLPLYHKHY ILFCTTVFTL LLLSIVILYC RIYSLVRTRS
edg3_human   TLGALPILGW NCLHNLPDCS TILPLYSKKY IAFCISIFTA ILVTIVILYA RIYFLVKSSS
edg5_human   VLGGLPILGW NCLGHLEACS TVLPLYAKHY VLCVVTIFSI ILLAIVALYV RIYCVVRSSH
edg8_human   LLGLLPALGW NCLGRLDACS TVLPLYAKAY VLFCVLAFVG ILAAICALYA RIYCQVRANA
edg6_human   LLGMLPLLGW NCLCAFDRCS SLLPLYSKRY ILFCLVIFAG VLATIMGLYG AIFRLVQASG
```

FIG. 1E

```
            241                                                                    300
edg2_human  MRMSRHSSGP R......RNR DTMMSLLKTV VIVLGAFIIC WTPGLVLLLL D.VCCP..QC
edg7_human  NVLSPHTSGS I......SRR RTPMKLMKTV MTVLGAFVVC WTPGLVVLLL DGLNCR..QC
edg4_human  QRMAEHVSCH P......RYR ETTLSLVKTV VIILGAFVVC WTPGQVVLLL DGLGCE..SC
edg1_human  RRLTFR.... .KNISKASRS SENVALLKTV IIVLSVFIAC WAPLFILLLL DV.GCKVKTC
edg3_human  RKVANH.... .NN......S ERSMALLRTV VIVVSVFIAC WSPLFILFLI DV.ACRVQAC
edg5_human  ADMA...... ..........A PQTLALLKTV TIVLGVFIVC WLPAFSILLL DY.ACPVHSC
edg8_human  RRLPARPGTA GTTSTRARRK PRSLALLRTL SVVLLAFVAC WGPLFLLLLL DV.ACPARTC
edg6_human  QKAP...... ...RPAARRK ARR..LLKTV LMILLAFLVC WGPLFGLLLA DVFGSNLWAQ 301                                                                    360
edg2_human  DVLAYEKFFL LLAEFNSAMN PIIYSYRDKE MSATFRQILC CQRSENPTGP TESSDRSASS
edg7_human  GVQHVKRNFL LLALLNSVVN PIIYSYKDED MYGTMKKMIC CFSQENP... ....ERRPSR
edg4_human  NVLAVEKYFL LLAEANSLVN AAVYSCRDAE MRRTFRRLLC CACLRQSTRE SVHYTSSAQG
edg1_human  DILFRAEYFL VLAVLNSGTN PIIYTLTNKE MRRAFIRIMS CCKCPSGD.. .........S
edg3_human  PILFKAQWFI VLAVLNSAMN PVIYTLASKE MRRAFFRLV. .CNC.LVR.. .........G
edg5_human  PILYKAHYFF AVSTLNSLLN PVIYTWRSRD LRREVLRPLQ CWRPGVGV.. .........Q
edg8_human  PVLLQADPFL GLAMANSLLN PIIYTLTNRD LRHALLRLVC CGRHSCGRDP SGS..QQSAS
edg6_human  EYLRGMDWIL ALAVLNSAVN PIIYSFRSRE VCRAVLSFLC CGCLRLGMRG PGDCLARAVE 361                                                         418
edg2_human  LNHTILAGVH SNDHSVV--- ---------- ---------- ---------- --------
edg7_human  IPSTVLSRSD TGSQYIEDSI SQGAVCNKST S--------- ---------- --------
edg4_human  GASTRIMLPE NGHPLMTPPF SYLELQRYAA SNKSTAPDDL WVLLAQPNQQ D-------
edg1_human  AGKFKRPIIA GMEFSRSK.. .SDNSSHPQK DEGDNPETIM SSGNVNSSS- --------
edg3_human  RGARASPIQP ALDPSRSKSS SSNNSSHSPK VKEDLPHTDP SSCIMDKNAA LQNGIFCN
edg5_human  GRRRVGTPGH HLLPLRSSSS LERGMHMPTS PTFLEGNTVV ---------- --------
edg8_human  AAEASGGLRR CLPPGLDGSF SGSERSSPQR DGLDTSGSTG SPGAPTAART LVSEPAAD
edg6_human  AHSGASTTDS SLRP.RDSFR GSRSLSFRMR EPLSSISSVR SI-------- --------
```

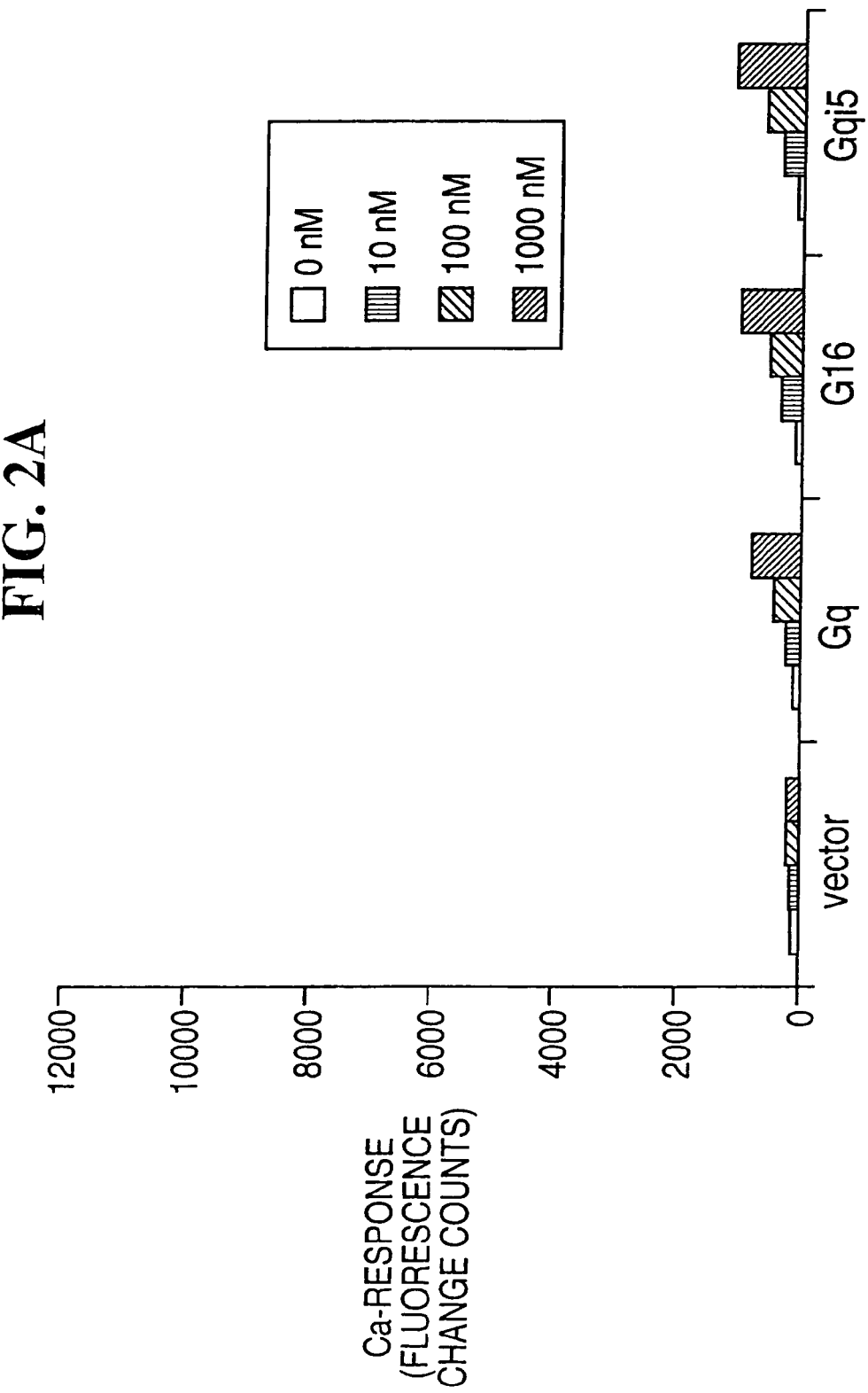

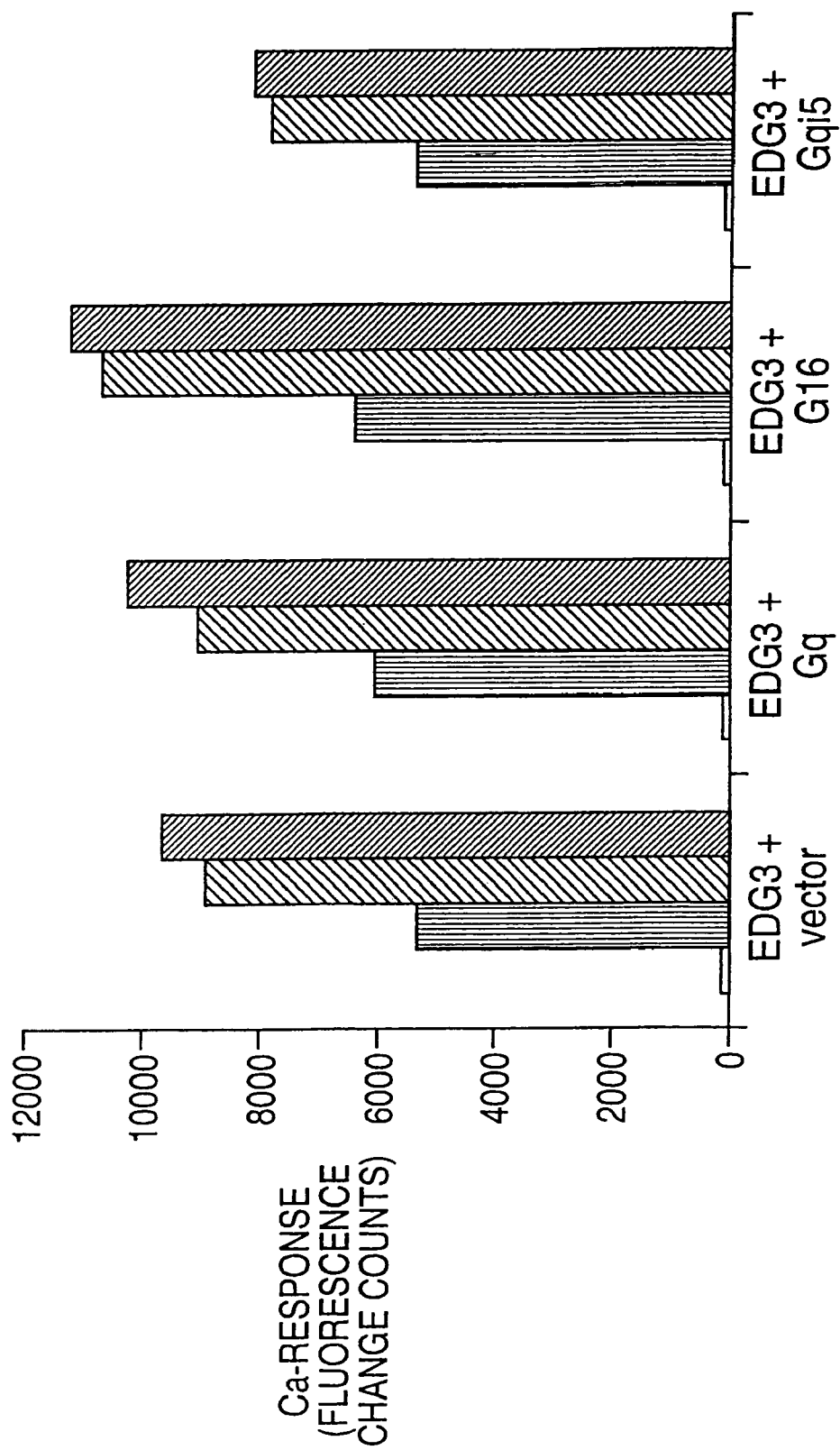

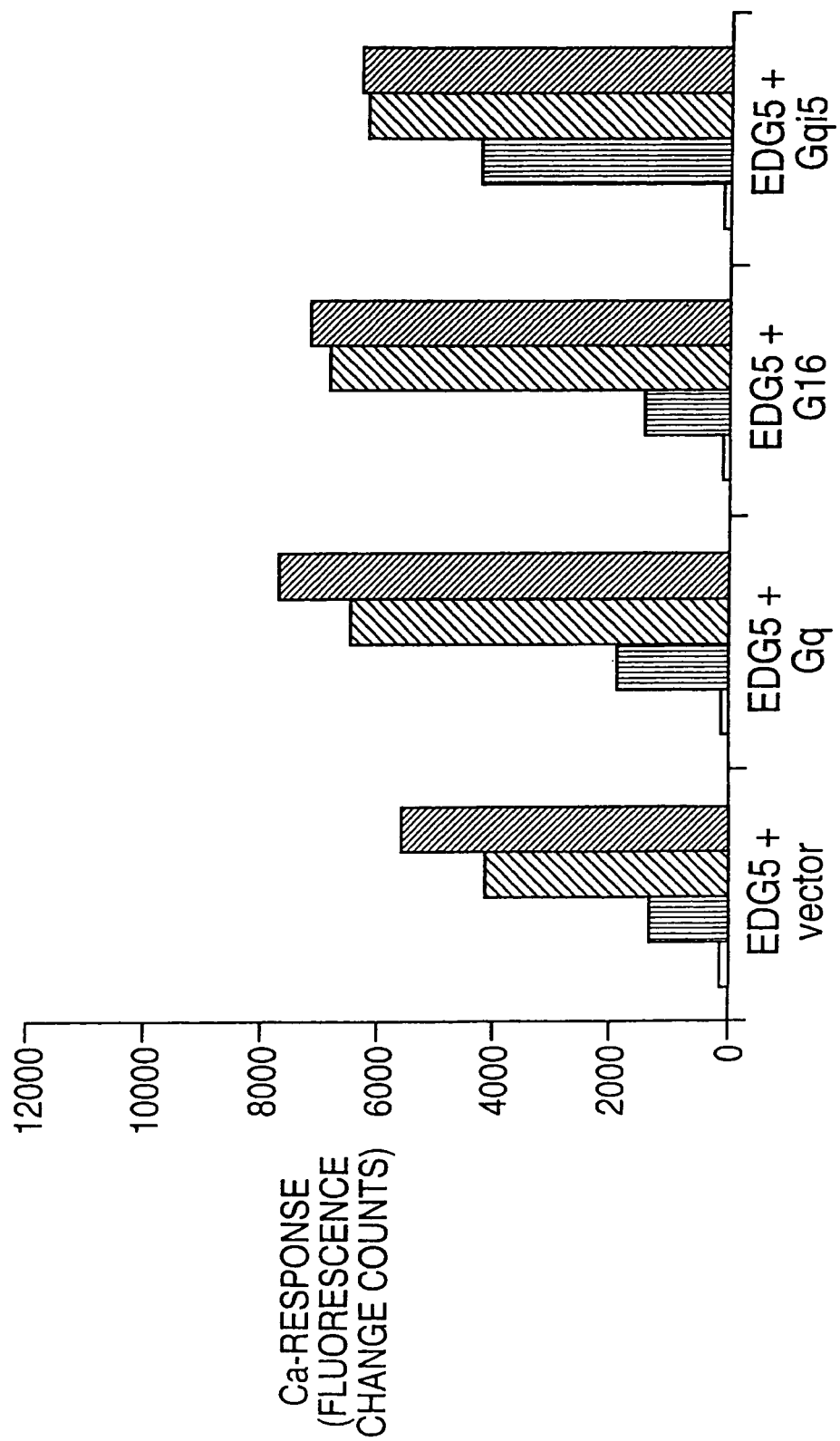

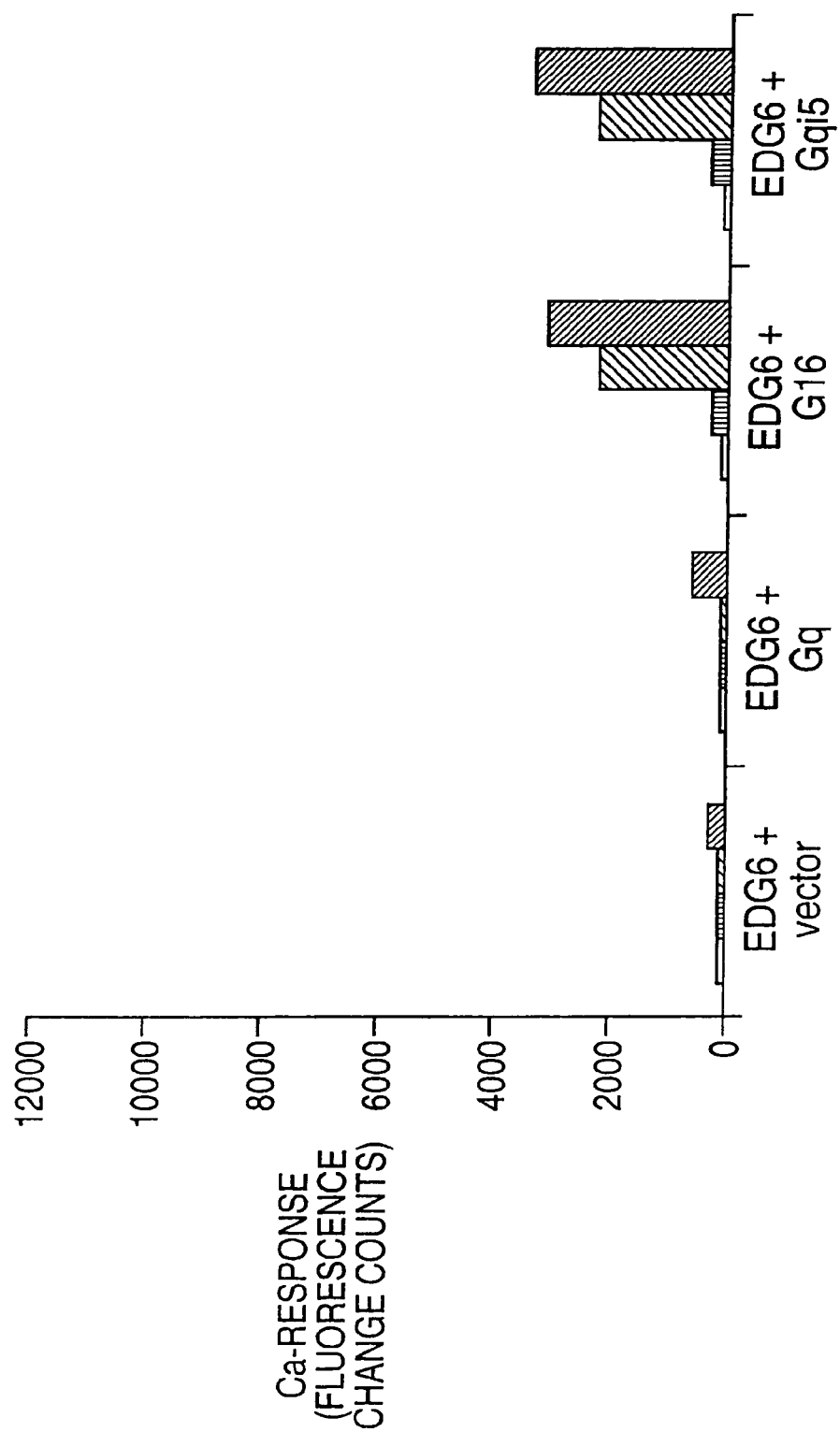

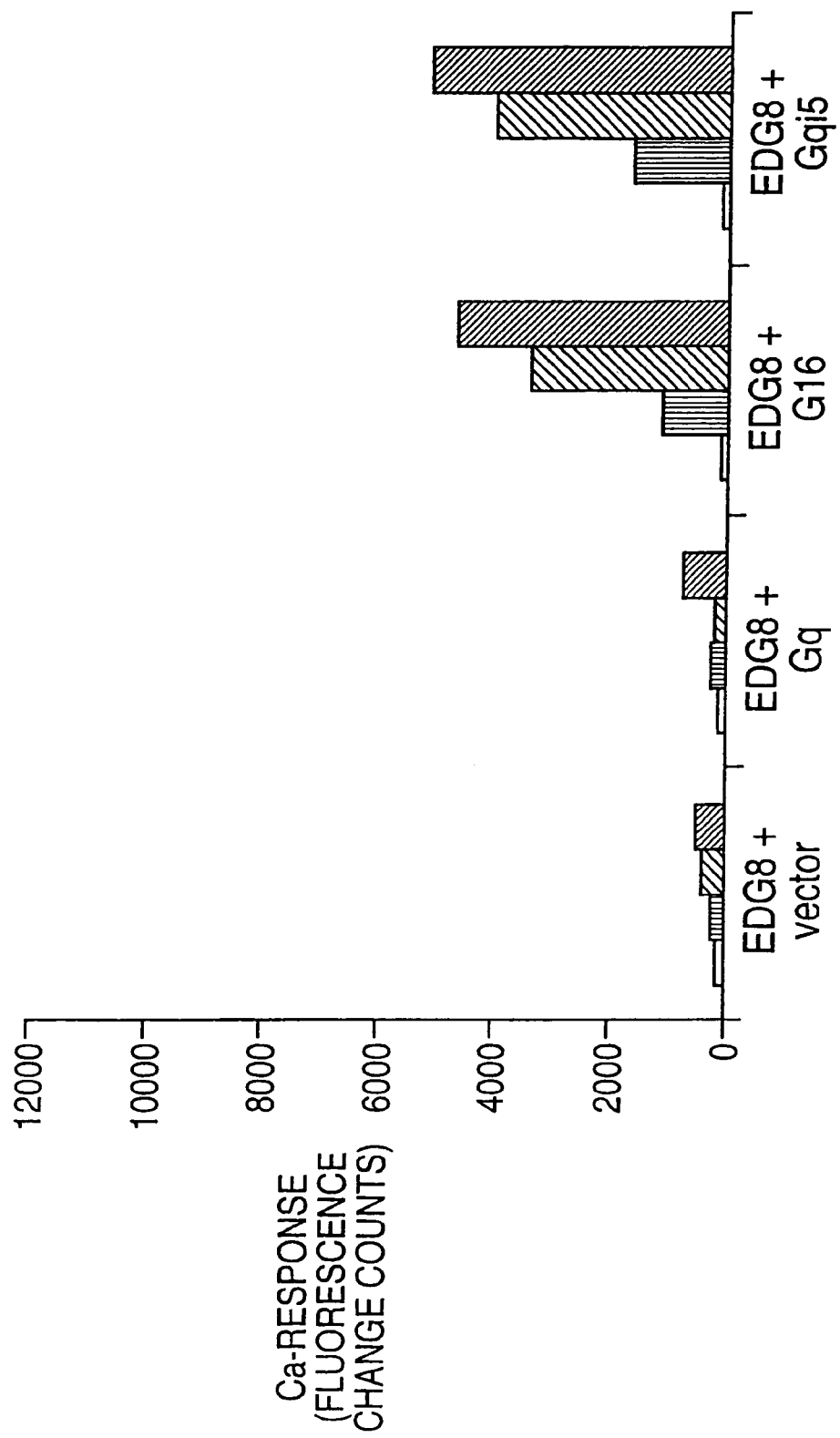

qi5 background rEDG8

FIG. 6C

Fluorescence Change counts

| Wells | Lipid | background | rEDG8 | stand. response |
|---|---|---|---|---|
| H10-H12 | 1µM S1P | 0 | 5196 | 5196 |
| F5 | 1µM LPA | 5893 | 4327 | -1566 |
| F3 | 1µM cPAF | 1017 | 1570 | 553 |
| E10 | 1µM EPA PAF | 0 | 1354 | 1354 |
| E9 | 1µM AA PAF | 0 | 3121 | 3121 |
| E8 | 1µM Enantio PAF | 0 | 3883 | 3883 |
| E7 | 1µM paf C18:1 | 1256 | 3765 | 2509 |
| E6 | 1µM Lyso PAF | 0 | 2421 | 2421 |
| D8 | 1µM dhS1P | 0 | 5144 | 5144 |
| D6 | 1µM S1P | 0 | 3672 | 3672 | qi5 background in HEK hEDG8

FIG. 7C

Fluorescence change counts

| Wells | Lipid | background | hEDG8 | stand. response |
|---|---|---|---|---|
| H10-H12 | 1µM S1P | 3696 | 9493 | 5797 |
| F5 | 1µM LPA | 18004 | 16333 | -1671 |
| D8 | 1µM dhS1P | 1683 | 4522 | 2839 |
| D6 | 1µM S1P | 2273 | 5605 | 3332 |

1) S1P 2) Leukotrien B4 3) 2 DHLA PAF 4) $C_2$ Dihydroceramide
5) 15(S)-HEDE 6) PAF C16 7) 16,16-Dimethyl $PGE_2$
8) 12(R)-HETE 9) 8-Epi-$PGF_{2\alpha}$ 10) Leukotoxin A

SEQUENCE LISTING

<160> NUMBER OF SEQ ID NOS: 9

<210> SEQ ID NO 1
<211> LENGTH: 1197
<212> TYPE: DNA
<213> ORGANISM: Homo sapiens
<220> FEATURE:
<221> NAME/KEY: CDS
<222> LOCATION: (1)..(1194)
<223> OTHER INFORMATION:

<400> SEQUENCE: 1

```
atg gag tcg ggg ctg ctg cgg ccg gcg ccg gtg agc gag gtc atc gtc      48
Met Glu Ser Gly Leu Leu Arg Pro Ala Pro Val Ser Glu Val Ile Val
1               5                   10                  15 ctg cat tac aac tac acc ggc aag ctc cgc ggt gcg cgc tac cag ccg      96
Leu His Tyr Asn Tyr Thr Gly Lys Leu Arg Gly Ala Arg Tyr Gln Pro
                20                  25                  30 ggt gcc ggc ctg cgc gcc gac gcc gtg gtg tgc ctg gcg gtg tgc gcc     144
Gly Ala Gly Leu Arg Ala Asp Ala Val Val Cys Leu Ala Val Cys Ala
            35                  40                  45 ttc atc gtg cta gag aat cta gcc gtg ttg ttg gtg ctc gga cgc cac     192
Phe Ile Val Leu Glu Asn Leu Ala Val Leu Leu Val Leu Gly Arg His
        50                  55                  60 ccg cgc ttc cac gct ccc atg ttc ctc ctg ggc agc ctc acg ttg         240
Pro Arg Phe His Ala Pro Met Phe Leu Leu Leu Gly Ser Leu Thr Leu
65                  70                  75                  80 tcg gat ctg ctg gca ggc gcc gcc tac gcc gcc aac atc cta ctg tcg     288
Ser Asp Leu Leu Ala Gly Ala Ala Tyr Ala Ala Asn Ile Leu Leu Ser
                85                  90                  95 ggg ccg ctc acg ctg aaa ctg tcc ccc gcg ctc tgg ttc gca cgg gag     336
Gly Pro Leu Thr Leu Lys Leu Ser Pro Ala Leu Trp Phe Ala Arg Glu
            100                 105                 110 gga ggc gtc ttc gtg gca ctc act gcg tcc gtg ctg agc ctc ctg gcc     384
Gly Gly Val Phe Val Ala Leu Thr Ala Ser Val Leu Ser Leu Leu Ala
        115                 120                 125 atc gcg ctg gag cgc agc ctc acc atg gcg cgc agg ggg ccc gcg ccc     432
Ile Ala Leu Glu Arg Ser Leu Thr Met Ala Arg Arg Gly Pro Ala Pro
130                 135                 140 gtc tcc agt cgg ggg cgc acg ctg gca atg gca gcc gcg gcc tgg ggc     480
Val Ser Ser Arg Gly Arg Thr Leu Ala Met Ala Ala Ala Ala Trp Gly
145                 150                 155                 160 gtg tcg ctg ctc ctc ggg ctc ctg cca gcg ctg ggc tgg aat tgc ctg     528
Val Ser Leu Leu Leu Gly Leu Leu Pro Ala Leu Gly Trp Asn Cys Leu
                165                 170                 175 ggt cgc ctg gac gct tgc tcc act gtc ttg ccg ctc tac gcc aag gcc     576
Gly Arg Leu Asp Ala Cys Ser Thr Val Leu Pro Leu Tyr Ala Lys Ala
            180                 185                 190 tac gtg ctc ttc tgc gtg ctc gcc ttc gtg ggc atc ctg gcc gct atc     624
Tyr Val Leu Phe Cys Val Leu Ala Phe Val Gly Ile Leu Ala Ala Ile
        195                 200                 205 tgt gca ctc tac gcg cgc atc tac tgc cag gta cgc gcc aac gcg cgg     672
Cys Ala Leu Tyr Ala Arg Ile Tyr Cys Gln Val Arg Ala Asn Ala Arg
    210                 215                 220 cgc ctg ccg gca cgg ccc ggg act gcg ggg acc acc tcg acc cgg gcg     720
Arg Leu Pro Ala Arg Pro Gly Thr Ala Gly Thr Thr Ser Thr Arg Ala
225                 230                 235                 240 cgt cgc aag ccg cgc tcg ctg gcc ttg ctg cgc acg ctc agc gtg gtg     768
Arg Arg Lys Pro Arg Ser Leu Ala Leu Leu Arg Thr Leu Ser Val Val
                245                 250                 255 ctc ctg gcc ttt gtg gca tgt tgg ggc ccc ctc ttc ctg ctg ttg         816
Leu Leu Ala Phe Val Ala Cys Trp Gly Pro Leu Phe Leu Leu Leu Leu
            260                 265                 270 ctc gac gtg gcg tgc ccg gcg cgc acc tgt cct gta ctc ctg cag gcc     864
Leu Asp Val Ala Cys Pro Ala Arg Thr Cys Pro Val Leu Leu Gln Ala
        275                 280                 285 gat ccc ttc ctg gga ctg gcc atg gcc aac tca ctt ctg aac ccc atc     912
Asp Pro Phe Leu Gly Leu Ala Met Ala Asn Ser Leu Leu Asn Pro Ile
    290                 295                 300
```

```
atc tac acg ctc acc aac cgc gac ctg cgc cac gcg ctc ctg cgc ctg      960
Ile Tyr Thr Leu Thr Asn Arg Asp Leu Arg His Ala Leu Leu Arg Leu
305                 310                 315                 320 gtc tgc tgc gga cgc cac tcc tgc ggc aga gac ccg agt ggc tcc cag     1008
Val Cys Cys Gly Arg His Ser Cys Gly Arg Asp Pro Ser Gly Ser Gln
            325                 330                 335 cag tcg gcg agc gcg gct gag gct tcc ggg ggc ctg cgc cgc tgc ctg     1056
Gln Ser Ala Ser Ala Ala Glu Ala Ser Gly Gly Leu Arg Arg Cys Leu
            340                 345                 350 ccc ccg ggc ctt gat ggg agc ttc agc ggc tcg gag cgc tca tcg ccc     1104
Pro Pro Gly Leu Asp Gly Ser Phe Ser Gly Ser Glu Arg Ser Ser Pro
            355                 360                 365 cag cgc gac ggg ctg gac acc agc ggc tcc aca ggc agc ccc ggt gca     1152
Gln Arg Asp Gly Leu Asp Thr Ser Gly Ser Thr Gly Ser Pro Gly Ala
370                 375                 380 ccc aca gcc gcc cgg act ctg gta tca gaa ccg gct gca gac tga         1197
Pro Thr Ala Ala Arg Thr Leu Val Ser Glu Pro Ala Ala Asp
385                 390                 395

<210> SEQ ID NO 2
<211> LENGTH: 398
<212> TYPE: PRT
<213> ORGANISM: Homo sapiens

<400> SEQUENCE: 2

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255
```

```
Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
            275                 280                 285

Asp Pro Phe Leu Gly Leu Ala Met Ala Asn Ser Leu Leu Asn Pro Ile
            290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
            355                 360                 365

Gln Arg Asp Gly Leu Asp Thr Ser Gly Ser Thr Gly Ser Pro Gly Ala
            370                 375                 380

Pro Thr Ala Ala Arg Thr Leu Val Ser Glu Pro Ala Ala Asp
385                 390                 395

<210> SEQ ID NO 3
<211> LENGTH: 364
<212> TYPE: PRT
<213> ORGANISM: Homo sapiens

<400> SEQUENCE: 3

Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
            20                  25                  30

Phe Tyr Asn Arg Ser Gly Lys His Leu Ala Thr Glu Trp Asn Thr Val
            35                  40                  45

Ser Lys Leu Val Met Gly Leu Gly Ile Thr Val Cys Ile Phe Ile Met
        50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
            115                 120                 125

Asp Thr Ser Leu Thr Ala Ser Val Ala Asn Leu Leu Ala Ile Ala Ile
            130                 135                 140

Glu Arg His Ile Thr Val Phe Arg Met Gln Leu His Thr Arg Met Ser
145                 150                 155                 160

Asn Arg Arg Val Val Val Val Ile Val Val Ile Trp Thr Met Ala Ile
                165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
            195                 200                 205

Phe Trp Ala Ile Phe Asn Leu Val Thr Phe Val Val Met Val Val Leu
            210                 215                 220

Tyr Ala His Ile Phe Gly Tyr Val Arg Gln Arg Thr Met Arg Met Ser
```

```
                     225                 230                 235                 240
Arg His Ser Ser Gly Pro Arg Arg Asn Arg Asp Thr Met Met Ser Leu
                245                 250                 255
Leu Lys Thr Val Val Ile Val Leu Gly Ala Phe Ile Ile Cys Trp Thr
            260                 265                 270
Pro Gly Leu Val Leu Leu Leu Asp Val Cys Cys Pro Gln Cys Asp
        275                 280                 285
Val Leu Ala Tyr Glu Lys Phe Phe Leu Leu Ala Glu Phe Asn Ser
    290                 295                 300
Ala Met Asn Pro Ile Ile Tyr Ser Tyr Arg Asp Lys Glu Met Ser Ala
305                 310                 315                 320
Thr Phe Arg Gln Ile Leu Cys Cys Gln Arg Ser Glu Asn Pro Thr Gly
                325                 330                 335
Pro Thr Glu Ser Ser Asp Arg Ser Ala Ser Ser Leu Asn His Thr Ile
            340                 345                 350
Leu Ala Gly Val His Ser Asn Asp His Ser Val Val
            355                 360

<210> SEQ ID NO 4
<211> LENGTH: 353
<212> TYPE: PRT
<213> ORGANISM: Homo sapiens

<400> SEQUENCE: 4

Met Asn Glu Cys His Tyr Asp Lys His Met Asp Phe Phe Tyr Asn Arg
1               5                   10                  15
Ser Asn Thr Asp Thr Val Asp Asp Trp Thr Gly Thr Lys Leu Val Ile
            20                  25                  30
Val Leu Cys Val Gly Thr Phe Phe Cys Leu Phe Ile Phe Phe Ser Asn
        35                  40                  45
Ser Leu Val Ile Ala Ala Val Ile Lys Asn Arg Lys Phe His Phe Pro
    50                  55                  60
Phe Tyr Tyr Leu Leu Ala Asn Leu Ala Ala Ala Asp Phe Phe Ala Gly
65                  70                  75                  80
Ile Ala Tyr Val Phe Leu Met Phe Asn Thr Gly Pro Val Ser Lys Thr
                85                  90                  95
Leu Thr Val Asn Arg Trp Phe Leu Arg Gln Gly Leu Leu Asp Ser Ser
            100                 105                 110
Leu Thr Ala Ser Leu Thr Asn Leu Leu Val Ile Ala Val Glu Arg His
        115                 120                 125
Met Ser Ile Met Arg Met Arg Val His Ser Asn Leu Thr Lys Lys Arg
    130                 135                 140
Val Thr Leu Leu Ile Leu Leu Val Trp Ala Ile Ala Ile Phe Met Gly
145                 150                 155                 160
Ala Val Pro Thr Leu Gly Trp Asn Cys Leu Cys Asn Ile Ser Ala Cys
                165                 170                 175
Ser Ser Leu Ala Pro Ile Tyr Ser Arg Ser Tyr Leu Val Phe Trp Thr
            180                 185                 190
Val Ser Asn Leu Met Ala Phe Leu Ile Met Val Val Val Tyr Leu Arg
        195                 200                 205
Ile Tyr Val Tyr Val Lys Arg Lys Thr Asn Val Leu Ser Pro His Thr
    210                 215                 220
Ser Gly Ser Ile Ser Arg Arg Arg Thr Pro Met Lys Leu Met Lys Thr
225                 230                 235                 240
```

```
Val Met Thr Val Leu Gly Ala Phe Val Cys Trp Thr Pro Gly Leu
            245                 250                 255

Val Val Leu Leu Leu Asp Gly Leu Asn Cys Arg Gln Cys Gly Val Gln
                260                 265                 270

His Val Lys Arg Trp Phe Leu Leu Ala Leu Leu Asn Ser Val Val
            275                 280                 285

Asn Pro Ile Ile Tyr Ser Tyr Lys Asp Glu Asp Met Tyr Gly Thr Met
        290                 295                 300

Lys Lys Met Ile Cys Cys Phe Ser Gln Glu Asn Pro Glu Arg Arg Pro
305                 310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
            340                 345                 350

Ser

<210> SEQ ID NO 5
<211> LENGTH: 382
<212> TYPE: PRT
<213> ORGANISM: Homo sapiens

<400> SEQUENCE: 5

Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
                20                  25                  30

Val Val Val Ala Leu Gly Leu Thr Val Ser Val Leu Val Leu Leu
            35                  40                  45

Thr Asn Leu Leu Val Ile Ala Ala Ile Ala Ser Asn Arg Arg Phe His
        50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Phe Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255
```

-continued

Gly Gln Val Val Leu Leu Asp Gly Leu Gly Cys Glu Ser Cys Asn
         260             265             270

Val Leu Ala Val Glu Lys Tyr Phe Leu Leu Ala Glu Ala Asn Ser
         275             280             285

Leu Val Asn Ala Ala Val Tyr Ser Cys Arg Asp Ala Glu Met Arg Arg
         290             295             300

Thr Phe Arg Arg Leu Leu Cys Cys Ala Cys Leu Arg Gln Ser Thr Arg
305                 310             315                 320

Glu Ser Val His Tyr Thr Ser Ser Ala Gln Gly Gly Ala Ser Thr Arg
                 325             330             335

Ile Met Leu Pro Glu Asn Gly His Pro Leu Met Thr Pro Pro Phe Ser
             340             345             350

Tyr Leu Glu Leu Gln Arg Tyr Ala Ala Ser Asn Lys Ser Thr Ala Pro
             355             360             365

Asp Asp Leu Trp Val Leu Leu Ala Gln Pro Asn Gln Gln Asp
             370             375             380

<210> SEQ ID NO 6
<211> LENGTH: 381
<212> TYPE: PRT
<213> ORGANISM: Homo sapiens

<400> SEQUENCE: 6

Met Gly Pro Thr Ser Val Pro Leu Val Lys Ala His Arg Ser Ser Val
1               5               10              15

Ser Asp Tyr Val Asn Tyr Asp Ile Ile Val Arg His Tyr Asn Tyr Thr
             20              25              30

Gly Lys Leu Asn Ile Ser Ala Asp Lys Glu Asn Ser Ile Lys Leu Thr
         35              40              45

Ser Val Val Phe Ile Leu Ile Cys Cys Phe Ile Ile Leu Glu Asn Ile
     50              55              60

Phe Val Leu Leu Thr Ile Trp Lys Thr Lys Lys Phe His Arg Pro Met
65              70              75              80

Tyr Tyr Phe Ile Gly Asn Leu Ala Leu Ser Asp Leu Leu Ala Gly Val
             85              90              95

Ala Tyr Thr Ala Asn Leu Leu Leu Ser Gly Ala Thr Thr Tyr Lys Leu
             100             105             110

Thr Pro Ala Gln Trp Phe Leu Arg Glu Gly Ser Met Phe Val Ala Leu
         115             120             125

Ser Ala Ser Val Phe Ser Leu Leu Ala Ile Ala Ile Glu Arg Tyr Ile
     130             135             140

Thr Met Leu Lys Met Lys Leu His Asn Gly Ser Asn Asn Phe Arg Leu
145             150             155             160

Phe Leu Leu Ile Ser Ala Cys Trp Val Ile Ser Leu Ile Leu Gly Gly
             165             170             175

Leu Pro Ile Met Gly Trp Asn Cys Ile Ser Ala Leu Ser Ser Cys Ser
             180             185             190

Thr Val Leu Pro Leu Tyr His Lys His Tyr Ile Leu Phe Cys Thr Thr
         195             200             205

Val Phe Thr Leu Leu Leu Leu Ser Ile Val Ile Leu Tyr Cys Arg Ile
     210             215             220

Tyr Ser Leu Val Arg Thr Arg Ser Arg Arg Leu Thr Phe Arg Lys Asn
225             230             235             240

Ile Ser Lys Ala Ser Arg Ser Ser Glu Asn Val Ala Leu Leu Lys Thr
             245             250             255

```
Val Ile Ile Val Leu Ser Val Phe Ile Ala Cys Trp Ala Pro Leu Phe
            260                 265                 270

Ile Leu Leu Leu Asp Val Gly Cys Lys Val Lys Thr Cys Asp Ile
            275                 280                 285

Leu Phe Arg Ala Glu Tyr Phe Leu Val Leu Ala Val Leu Asn Ser Gly
            290                 295                 300

Thr Asn Pro Ile Ile Tyr Thr Leu Thr Asn Lys Glu Met Arg Arg Ala
305                 310                 315                 320

Phe Ile Arg Ile Met Ser Cys Cys Lys Cys Pro Ser Gly Asp Ser Ala
                325                 330                 335

Gly Lys Phe Lys Arg Pro Ile Ile Ala Gly Met Glu Phe Ser Arg Ser
                340                 345                 350

Lys Ser Asp Asn Ser Ser His Pro Gln Lys Asp Glu Gly Asp Asn Pro
                355                 360                 365

Glu Thr Ile Met Ser Ser Gly Asn Val Asn Ser Ser Ser
370                 375                 380

<210> SEQ ID NO 7
<211> LENGTH: 378
<212> TYPE: PRT
<213> ORGANISM: Homo sapiens

<400> SEQUENCE: 7

Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
                20                  25                  30

Lys Glu Ala Ser Glu Gly Ser Thr Leu Thr Thr Val Leu Phe Leu Val
            35                  40                  45

Ile Cys Ser Phe Ile Val Leu Glu Asn Leu Met Val Leu Ile Ala Ile
        50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
            115                 120                 125

Leu Leu Ala Ile Ala Ile Glu Arg His Leu Thr Met Ile Lys Met Arg
        130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
                180                 185                 190

Ser Lys Lys Tyr Ile Ala Phe Cys Ile Ser Ile Phe Thr Ala Ile Leu
            195                 200                 205

Val Thr Ile Val Ile Leu Tyr Ala Arg Ile Tyr Phe Leu Val Lys Ser
        210                 215                 220

Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
```

```
                   245                 250                 255
Ser Pro Leu Phe Ile Leu Phe Leu Ile Asp Val Ala Cys Arg Val Gln
                260                 265                 270

Ala Cys Pro Ile Leu Phe Lys Ala Gln Trp Phe Ile Val Leu Ala Val
            275                 280                 285

Leu Asn Ser Ala Met Asn Pro Val Ile Tyr Thr Leu Ala Ser Lys Glu
        290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Asn Asn Ser Ser His Ser Pro Lys Val Lys
            340                 345                 350

Glu Asp Leu Pro His Thr Asp Pro Ser Ser Cys Ile Met Asp Lys Asn
        355                 360                 365

Ala Ala Leu Gln Asn Gly Ile Phe Cys Asn
        370                 375

<210> SEQ ID NO 8
<211> LENGTH: 353
<212> TYPE: PRT
<213> ORGANISM: Homo sapiens

<400> SEQUENCE: 8

Met Gly Ser Leu Tyr Ser Glu Tyr Leu Asn Pro Asn Lys Val Gln Glu
1               5                   10                  15

His Tyr Asn Tyr Thr Lys Glu Thr Leu Glu Thr Gln Glu Thr Thr Ser
                20                  25                  30

Arg Gln Val Ala Ser Ala Phe Ile Val Ile Leu Cys Cys Ala Ile Val
            35                  40                  45

Val Glu Asn Leu Leu Val Leu Ile Ala Val Ala Arg Asn Ser Lys Phe
        50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Leu Ile Gly Ala Ser Trp Leu Ile Ser Leu
145                 150                 155                 160

Val Leu Gly Gly Leu Pro Ile Leu Gly Trp Asn Cys Leu Gly His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Ile Ile Leu Ala Ile Val Ala Leu
        195                 200                 205

Tyr Val Arg Ile Tyr Cys Val Val Arg Ser Ser His Ala Asp Met Ala
    210                 215                 220

Ala Pro Gln Thr Leu Ala Leu Leu Lys Thr Val Thr Ile Val Leu Gly
225                 230                 235                 240
```

```
Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Phe Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Val Gly Thr
305                 310                 315                 320

Pro Gly His His Leu Leu Pro Leu Arg Ser Ser Ser Leu Glu Arg
                325                 330                 335

Gly Met His Met Pro Thr Ser Pro Thr Phe Leu Glu Gly Asn Thr Val
                340                 345                 350

Val

<210> SEQ ID NO 9
<211> LENGTH: 384
<212> TYPE: PRT
<213> ORGANISM: Homo sapiens

<400> SEQUENCE: 9

Met Asn Ala Thr Gly Thr Pro Val Ala Pro Glu Ser Cys Gln Gln Leu
1               5                   10                  15

Ala Ala Gly Gly His Ser Arg Leu Ile Val Leu His Tyr Asn His Ser
            20                  25                  30

Gly Arg Leu Ala Gly Arg Gly Gly Pro Glu Asp Gly Gly Leu Gly Ala
        35                  40                  45

Leu Arg Gly Leu Ser Val Ala Ala Ser Cys Leu Val Val Leu Glu Asn
    50                  55                  60

Leu Leu Val Leu Ala Ala Ile Thr Ser His Met Arg Ser Arg Arg Trp
65                  70                  75                  80

Val Tyr Tyr Cys Leu Val Asn Ile Thr Leu Ser Asp Leu Leu Thr Gly
                85                  90                  95

Ala Ala Tyr Leu Ala Asn Val Leu Leu Ser Gly Ala Arg Thr Phe Arg
            100                 105                 110

Leu Ala Pro Ala Gln Trp Phe Leu Arg Glu Gly Leu Leu Phe Thr Ala
        115                 120                 125

Leu Ala Ala Ser Thr Phe Ser Leu Leu Phe Thr Ala Gly Glu Arg Phe
    130                 135                 140

Ala Thr Met Val Arg Pro Val Ala Glu Ser Gly Ala Thr Lys Thr Ser
145                 150                 155                 160

Arg Val Tyr Gly Phe Ile Gly Leu Cys Trp Leu Leu Ala Ala Leu Leu
                165                 170                 175

Gly Met Leu Pro Leu Leu Gly Trp Asn Cys Leu Cys Ala Phe Asp Arg
            180                 185                 190

Cys Ser Ser Leu Leu Pro Leu Tyr Ser Lys Arg Tyr Ile Leu Phe Cys
        195                 200                 205

Leu Val Ile Phe Ala Gly Val Leu Ala Thr Ile Met Gly Leu Tyr Gly
    210                 215                 220

Ala Ile Phe Arg Leu Val Gln Ala Ser Gly Gln Lys Ala Pro Arg Pro
225                 230                 235                 240

Ala Ala Arg Arg Lys Ala Arg Arg Leu Leu Lys Thr Val Leu Met Ile
                245                 250                 255
```

-continued

```
Leu Leu Ala Phe Leu Val Cys Trp Gly Pro Leu Phe Gly Leu Leu Leu
            260             265             270

Ala Asp Val Phe Gly Ser Asn Leu Trp Ala Gln Glu Tyr Leu Arg Gly
            275             280             285

Met Asp Trp Ile Leu Ala Leu Ala Val Leu Asn Ser Ala Val Asn Pro
        290             295             300

Ile Ile Tyr Ser Phe Arg Ser Arg Glu Val Cys Arg Ala Val Leu Ser
305             310             315             320

Phe Leu Cys Cys Gly Cys Leu Arg Leu Gly Met Arg Gly Pro Gly Asp
            325             330             335

Cys Leu Ala Arg Ala Val Glu Ala His Ser Gly Ala Ser Thr Thr Asp
            340             345             350

Ser Ser Leu Arg Pro Arg Asp Ser Phe Arg Gly Ser Arg Ser Leu Ser
            355             360             365

Phe Arg Met Arg Glu Pro Leu Ser Ser Ile Ser Ser Val Arg Ser Ile
            370             375             380
```

EDG8 RECEPTOR, ITS PREPARATION AND USE

This application is a divisional of U.S. Ser. No. 09/842,316 filed on Apr. 26, 2001, now abandoned which claims priority to European Application No. 108858.2, filed Apr. 26, 2000, and European Application No. 116589.3, filed Aug. 1, 2000, the disclosures of which are hereby incorporated by reference in their entireties.

FIELD OF THE INVENTION

The present invention relates to newly identified human EDG8 receptors, polynucleotides encoding this receptor, polypeptides encoded by such polynucleotides, the preparation and the use of such polynucleotides and polypeptides.

BACKGROUND OF THE INVENTION

In an effort to identify new G-protein coupled receptors of the EDG (endothelial differentiation gene)-family a novel member of the EDG-family of G-protein coupled receptors, Human EDG8, was identified. The full-length clone was isolated and studies on chromosomal mapping, tissue expression and identification as a functional cellular receptor for sphingosine 1-phosphate were performed. Taken together, the data provide compelling evidence that EDG8 is the fifth receptor for sphingosine 1-phosphate, exclusively expressed in peripheral tissues, its presence in endothelial cells being responsible for the broad tissue distribution.

The lysolipid phosphate mediators lysophosphatidic acid (LPA) and sphingosin 1-phosphate (S1P) have attracted increasing attention as modulators of a variety of important biological functions (Moolenaar et al., Current Opinion in Cell Biol 9:168, 1997; Morris, Trends Pharmacol Sci 20:393, 1999; Lynch and Im, Trends in Pharmacol Sci 20:473, 1999) and their list of biological activities is continuously growing.

Among the biological responses to LPA is platelet aggregation (Jalink et al., Biochem Biophys Acta 1198:185, 1994; Siess et al., PNAS USA 96:6931, 1999; Gueguen et al., Biochemistry 38: 8440, 1999), smooth muscle contraction (Tokumura et al., Arch Int Pharmacodyn Ther 245:74, 1980), in vivo vasoactive effects (Tokumura et al., Res Comm Mol Pathol Pharmacol 90:96, 1995), chemotaxis (Jalink et al., PNAS USA 90:1857, 1993), expression of adhesion molecules (Lee et al., J Biol Chem 273:22105, 1998; Rizza et al., Laboratory Investigation 79:1227, 1999), increased tight junction permeability of endothelial cells (Schulze et al., J Neurochem 68:991, 1997), induction of stress fibers (Gohla et al., J Biol Chem 274:17901, 1998) and many others (for review see Moolenaar et al., Current Opinion in Cell Biol 9:168, 1997). The biochemical signalling events that mediate the cellular effects of LPA include stimulation of phospholipases, mobilization of intracellular $Ca^{2+}$, inhibition of adenylyl cyclase, activation of phosphatidylinositol 3-kinase, activation of the Ras-Raf-MAP kinase cascade and stimulation of Rho-GTPases (Moolenaar et al., Current Opinion in Cell Biol 9:168, 1997).

S1P, in particular, is implicated in cell proliferation, modulation of cell motility (reviewed in Hla et al., Biochem Pharm 58:201, 1999) induction/suppression of apoptosis (Hisano et al., Blood 93:4293, 1999; Xia et al., J Biol Chem 274:34499, 1999), angiogenesis (Lee et al., Cell 99:301, 1999), tumor invasiveness (Sadahira et al., PNAS USA 89:9686, 1992), platelet activation (Gueguen et al., Biochemistry 38:8440, 1999) and neurite retraction (Postma et al., EMBO J 15:2388, 1996). Cellular signalling by S1P involves activation of PLCβ and subsequent intracellular $Ca^{2+}$ release (van Koppen et al., J Biol Chem 271:2082, 1996; Meyer zu Heringdorf et al., Naunyn-Schmiedeberg's Arch Pharmacol 354:397, 1997; Yatomi et al., J Biol Chem 272:5291, 1997a; Noh et al., J Cell Physiol 176:412, 1998; Ancellin and Hla, J Biol Chem 274:18997, 1999), activation of MAP-kinases (Wu et al., J Biol Chem 270:11484, 1995; Lee et al., J Biol Chem 271:11272, 1996; An et al., J Biol Chem 275:288, 2000), activation of inward rectifying $K^+$-channels (van Koppen et al., J Biol Chem 271:2082, 1996; Bünemann et al., EMBO J 15:5527, 1996) and inhibition and/or activation of adenylyl cyclase (Lee et al., J Biol Chem 271:11272, 1996).

Both, LPA and S1P are recognized to signal cells through a set of G-protein coupled receptors (GPCRs) known as EDG (endothelial differentiation gene)-receptors. The EDG-family of GPCRs currently comprises seven human members (EDG1-7) that fall into two major groups depending on their preference for the activating lipid-ligand: EDG1, 3, 5 and 6 preferentially interact with S1P (Yatomi et al., J Biochem (Tokyo) 12:969, 1997; Lee et al., Science 279: 1552, 1998; Lee et al., J Biol Chem 273:22105, 1998; Ancellin and Hla, J Biol Chem 274:18997, 1999; Yamazaki et al., Biochem Biophys Res Commun 268:583, 2000; Van Brocklyn et al., Blood 95:2624, 2000), EDG2, 4 and 7 preferentially interact with LPA (An et al., J Biol Chem 273:7906, 1998; Im et al., Mol Pharmacol 57:753, 2000).

The assignment of specific biological functions to certain receptor subtypes is hampered by the fact that EDG receptors are expressed in an overlapping fashion (Rizza et al., Laboratory Investigation 79:1227, 1999; Lee et al., Cell 99:301, 1999), they activate multiple and in part redundant signal transduction pathways (Lee et al., J Biol Chem 271:11272, 1996; Ancellin and Hla, J Biol Chem 274:18997, 1999; Kon et al., J Biol Chem 274:23940, 1999; An et al., J Biol Chem 275:288, 2000), the selectivity for their activating ligands is not absolute (Lee et al., J Biol Chem 273:22105, 1998), and medicinal chemistry is only poorly developed in that specific antagonists for dissecting the pharmacology of the individual subtypes are not available yet.

An important step to shed more light on the biological role of the individual receptor subtypes would be to identify the complete set of receptors that respond to the phospholipid mediators S1P and LPA.

SUMMARY OF THE INVENTION

The present invention relates to newly identified human EDG8 receptors, polynucleotides encoding this receptor, polypeptides encoded by such polynucleotides and the preparation and the use thereof.

The present invention relates to an isolated polynucleotide comprising a nucleotide sequence that has at least 90% identity, preferably 95% or more, most preferably 98% identity to a nucleotide sequence encoding the polypeptide of SEQ ID NO:2 or the corresponding fragment thereof; or a nucleotide sequence complementary to said nucleotide sequence.

The present invention also relates to an isolated polynucleotide comprising a nucleotide sequence that has at least about 90% identity, preferably about 95% or more, most preferably about 98% identity to a nucleotide sequence encoding the polypeptide of SEQ ID NO:2 or the corresponding fragment thereof; or a nucleotide sequence complementary to said nucleotide sequence.

Preferably, the polynucleotide is DNA or RNA. The nucleotide sequence of the polynucleotide is at least 90% or about 90% identical to that contained in SEQ ID NO:1; preferably 95% or about 95% or more, most preferred 98% or about 98% or more identical to SEQ ID NO:1. In another embodiment, the polynucleotide has the nucleotide sequence SEQ ID NO:1. In another embodiment, the polynucleotide encodes the polypeptide of SEQ ID NO:2 or a fragment thereof. In a special embodiment, the polynucleotide is an allele of SEQ ID NO:1. Preferably, the polynucleotide has the same essential properties and/or biological functionality as human EDG8.

One characteristic of "functionality" or "biological functionality" is that the polynucleotide encodes for a S1P receptor; it responds to S1P and optionally also to related phospholipids like DMS 1P or LPA. By "functionality" is meant the molecule is a functional receptor for S1P, LPA, dHS1P and related lysophospholipid mediators. Such activity may be assayed using well known techniques in the art. One such assay employs assessment of ability of $Ca^{2+}$ mobilization in response to S1P mediated by the receptor, e.g., EDG8 or a functional fragment thereof, in CHO cell as set forth in the description of FIG. 2.

Another aspect of the invention relates to an expression system for the expression of EDG8. The EDG8 DNA or RNA molecule comprising an expression system wherein said expression system is capable of producing a polypeptide or a fragment thereof having at least 90% or about 90% identity, preferably 95% or about 95% or more, most preferred 98% or about 98% or more identity with a nucleotide sequence encoding the polypeptide of SEQ ID NO. 2 or said fragment when said expression system is present in a compatible host cell. Preferably, the expression system is a vector.

The invention relates to a host cell comprising the expression system.

In another aspect, the invention relates to a process for producing a human EDG8 polypeptide or a fragment thereof wherein a host cell comprising the expression system is cultured under conditions sufficient for the production of said polypeptide or fragment thereof. Preferably, the said polypeptide or fragment thereof is expressed at the surface of said cell.

The invention relates also to cells produced by this process.

The process preferably further includes recovering the polypeptide or fragment thereof from the culture.

In another aspect, the invention relates to a process for producing a cell which produces an EDG8 polypeptide or a fragment thereof comprising transforming or transfecting a host cell with the expression system such that the host cell, under appropriate culture conditions, produces a human EDG8 polypeptide or a fragment thereof.

Thus, in one embodiment, the invention relates to an isolated polynucleotide comprising a polynucleotide selected from the group consisting of:
 (a) a polynucleotide encoding the polypeptide consisting of the amino acid sequence of SEQ ID NO:2;
 (b) a polynucleotide consisting of SEQ ID NO:1;
 (c) a polynucleotide having at least about 90% sequence identity to the polynucleotide of (a) or (b).

In another embodiment, the invention relates to a fragment of the polynucleotide of SEQ ID NO:1. In yet another embodiment, the invention relates to a polynucleotide which is a complement of the above described polynucleotide.

Other embodiments relate to an expression vector comprising the isolated polynucleotide and a host cell comprising such expression vector. A further embodiment is a method of producing a polypeptide comprising SEQ ID NO:2 by culturing such host cell under conditions sufficient for the production of the polypeptide and recovering it from the culture. Another embodiment of the invention relates to a process for producing cells capable of expressing the above polypeptide comprising genetically transfecting or transforming cells with the above vector.

Another embodiment relates to an antibody that selectively binds a polypeptide comprising the amino acid sequence of SEQ ID NO:2 or a fragment of SEQ ID NO:2.

A further embodiment relates to a process for diagnosing a disease or a susceptibility to a disease related to expression or activity of human EDG8 polypeptide comprising:
 determining the presence or absence of mutation in the nucleotide sequence encoding human EDG8 polypeptide in the genome of the subject; and/or
 analyzing for the presence or amount of the human EDG8 polypeptide expression in a sample derived from the subject.

Another embodiment relates to a method for identifying compounds which bind to human EDG8 polypeptide comprising:
 a) contacting a cell containing the above described polynucleotides of the invention with a candidate compound; and
 b) assessing the ability of said candidate compound to bind to the cells. This method further includes determining whether the candidate compound effects a signal generated by activation of the human EDG8 polypeptide at the surface of the cell, wherein a candidate compound which effects production of the signal is identified as an agonist. In another embodiment, this method further includes determining whether the candidate compound effects a signal generated by activation of the human EDG8 polypeptide at the surface of the cell, wherein a candidate compound which effects production of the signal is identified as an antagonist.

Thus, the present invention relates to agonists and antagonists identified by the above described methods.

In yet another embodiment, the invention relates to a method of preparing a pharmaceutical composition comprising:
 a) identifying a compound which is an agonist or an antagonist of human EDG8,
 b) preparing the compound, and
 c) optionally mixing the compound with suitable additives and to pharmaceutical composition prepared by such method.

BRIEF DESCRIPTION OF THE DRAWINGS

FIGS. 1A and 1B: The nucleotide and deduced amino acid sequence of human EDG8. The deduced amino acid sequence (SEQ ID NO: 2) is shown below the nucleotide sequence (SEQ ID NO: 1) with the nucleotide positions indicated on the left.

FIGS. 1D and E: Alignment of the amino acid sequence of human EDG8 with the other EDG-family members. The amino acid sequence of human EDG8 (accession number AC011461) is compared with the EDG1–7 polypeptides (EDG1: accession number M 31210, EDG2: accession number U 80811, EDG3: accession number X 83864, EDG4: accession number AF 011466, EDG5: accession number AF 034780, EDG6: AJ 000479, EDG7: accession number AF 127138). The approximate boundaries of the seven putative transmembrane domains are boxed. Gaps are introduced to optimize the alignment.

FIGS. 2A–F: Mobilization of intracellular $Ca^{2+}$ by S1P (10, 100 and 1000 nM) mediated by the EDG1, 3, 5, 6 and 8 receptor in CHO cells, cotransfected with empty vector DNA as a control or the indicated G-protein α subunits.

A: S1P-induced $Ca^{2+}$-response in CHO cells transfected with vector DNA alone or the G protein α subunits Gq, G16 and Gqi5. B-F: S1P-induced $Ca^{2+}$-response in CHO cells transfected with the indicated EDG-receptor subtypes. Agonist-mediated changes of intracellular $Ca^{2+}$ were measured with the FLIPR using the $Ca^{2+}$-sensitive dye FLUO4 as described in Experimental procedures. Fluorescence of transfected cells loaded with FLUO4 was recorded before and after addition of S1P, applied in the indicated concentrations. Data are expressed as means of quadruplicate determinations in a single experiment. An additional experiment gave similar results.

Figure 3:
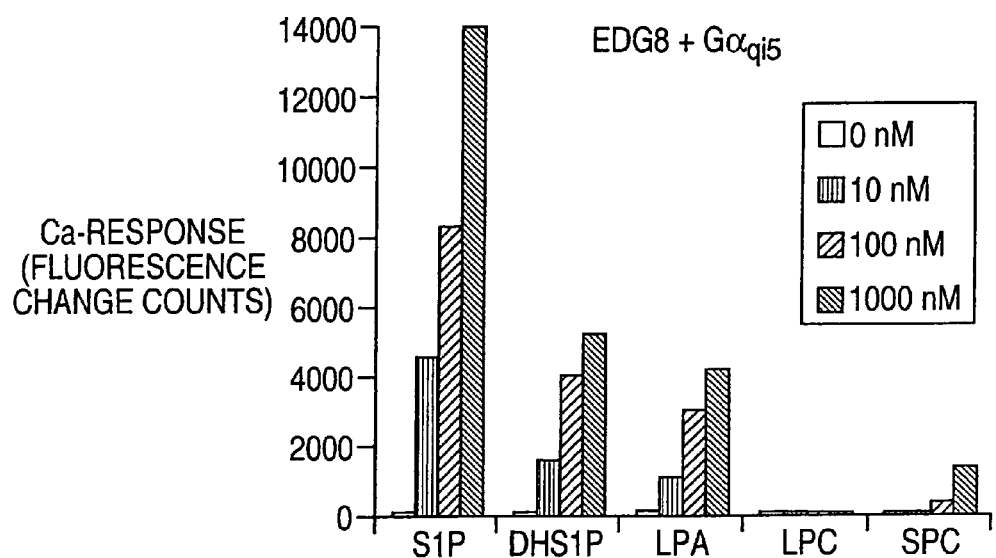
Figure 3:
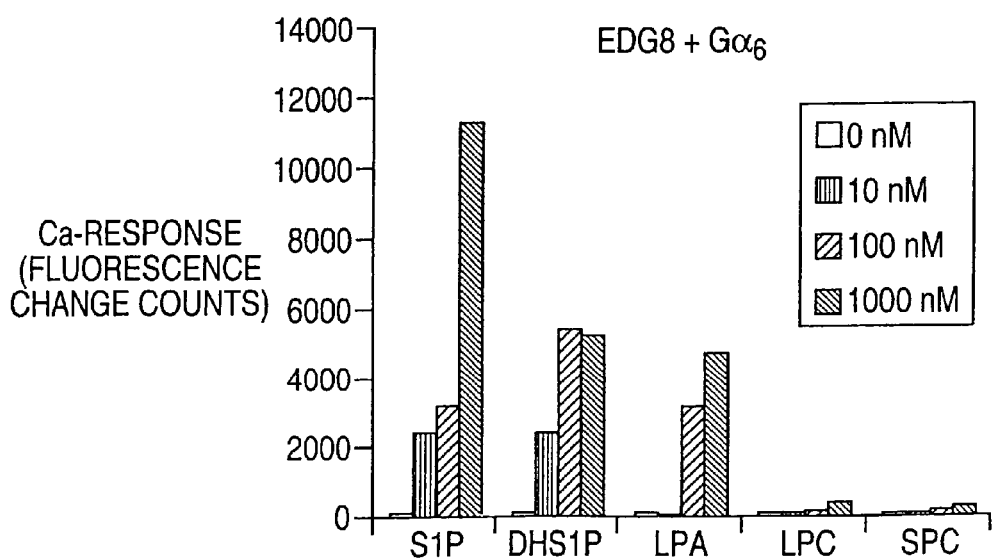

FIG. 3: Effects of S1P, LPA and related lysophospholipid mediators on EDG8-mediated increase in intracellular $Ca^{2+}$. CHO-cells were cotransfected with EDG8 and the G protein α subunits Gqi5 (upper panel) and G16 (lower panel) and rises in $[Ca^{2+}]_i$ were recorded with the FLIPR as described in Experimental procedures. The different lipids were applied in concentrations of 10, 100 and 1000 nM, respectively. Data are means of quadruplicate determinations of a representative experiment. Two additional experiments gave similar results.

Figure 4:
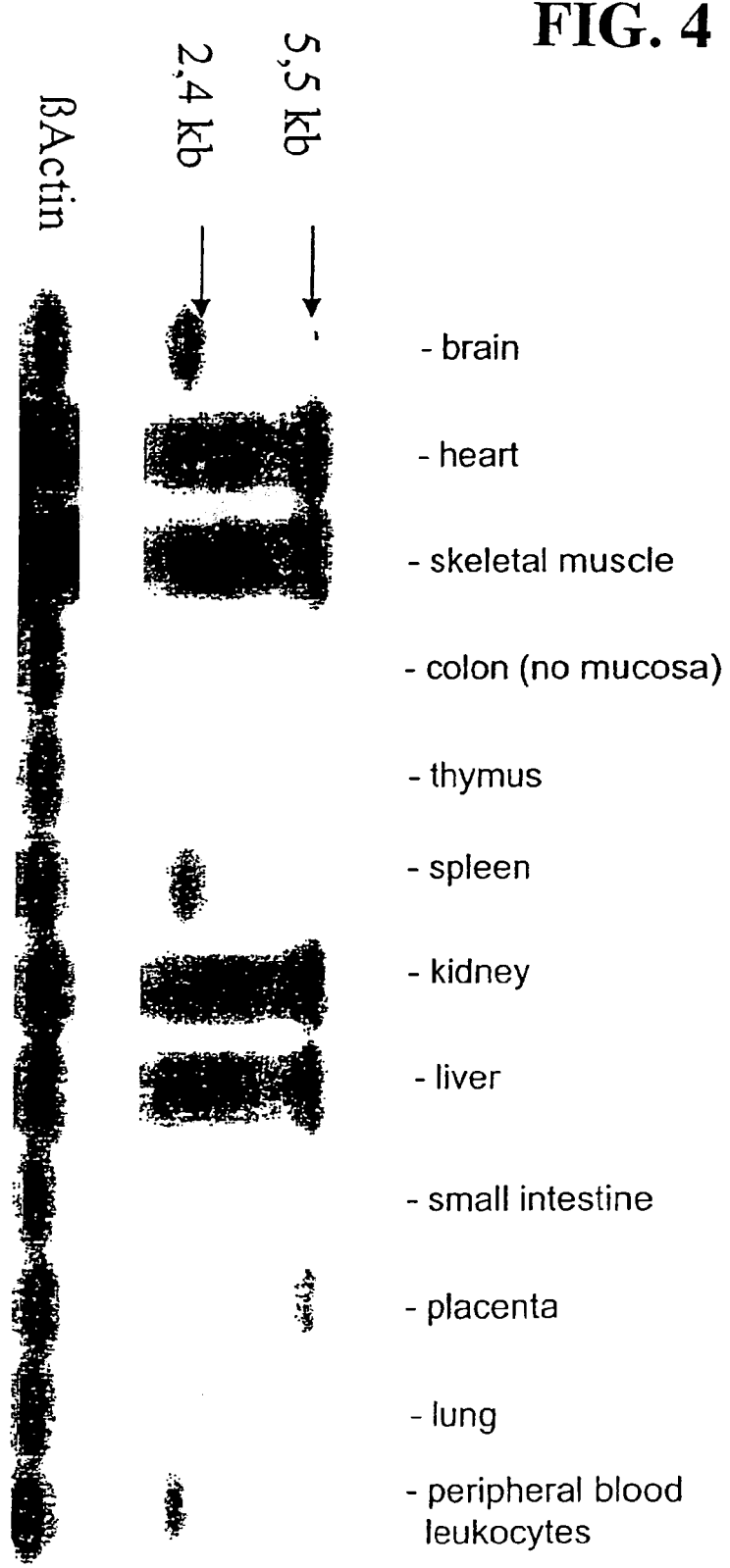

FIG. 4: Northern blot analysis of EDG8 in human tissues. Poly(A)+ RNA (1 µg) from various human tissues (human multiple tissue Northern blots, CLONTECH) was hybridized with probes specific to human EDG8 (upper panel) and β-actin (lower panel) on a nylon membrane. The origin of each RNA is indicated at the top, the molecular mass of standard markers in kilobases (kb) is shown on the left.

Figure 5A:
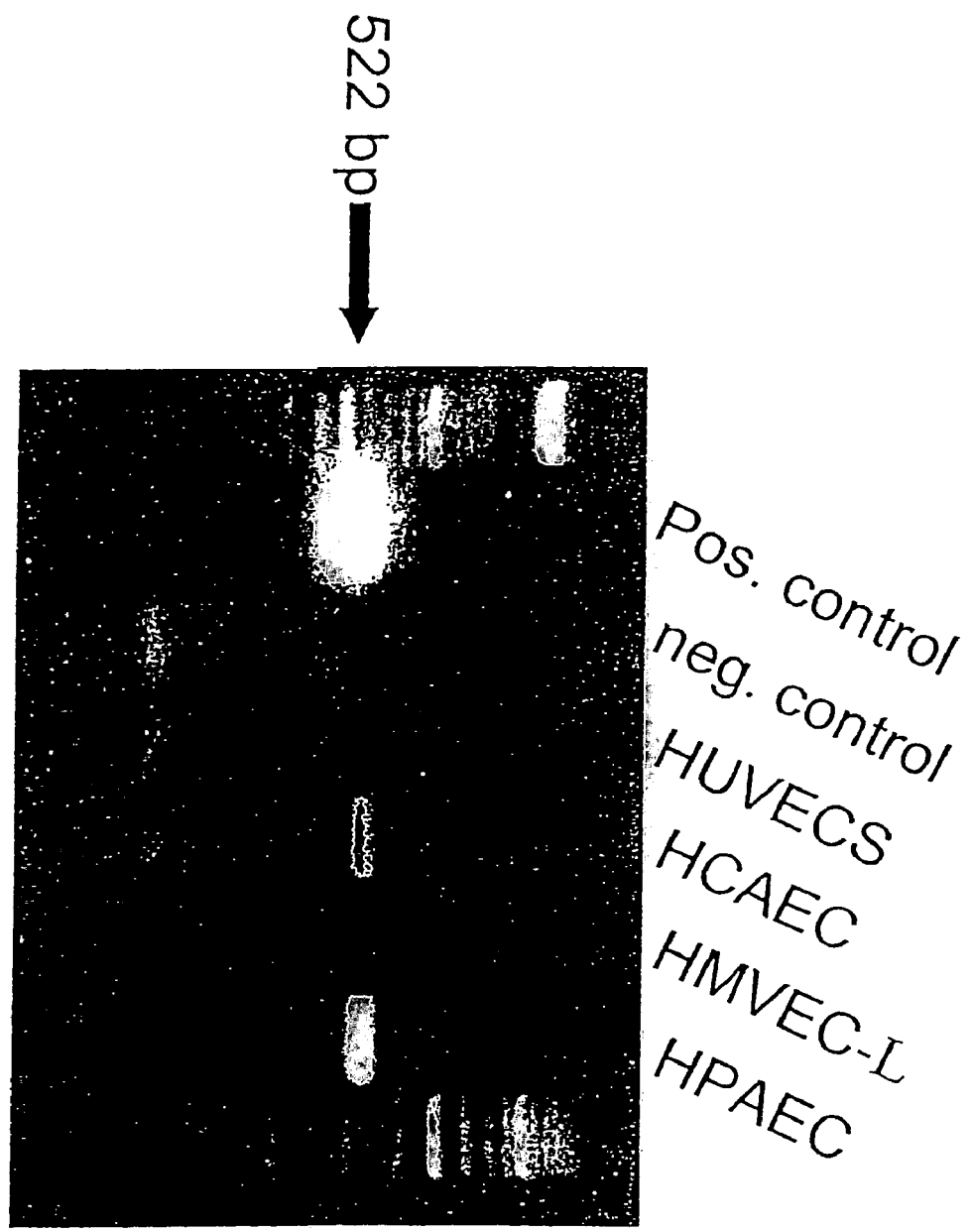

FIG. 5A: Reverse transcriptase-polymerase chain reaction (RT-PCR) analysis of EDG8 in different human endothelial cell lines (HUVECs: human umbilical vein endothelial cells; HCAEC: human coronary artery endothelial cells; HMVEC-L: human microvascular endothelial cells from lung; HPAEC: human pulmonary artery endothelial cells). EDG8-specific transcripts were detected in all endothelial cell lines. Agarose gel electrophoresis of the PCR products after 35 cycles of amplification with the GC-melt kit (as described in Experimental Procedures) is shown. Amplification with EDG8-specific primers yields a 522 bp EDG8-fragment as indicated by the arrow. The EDG8 plasmid served as a template for the positive control, $H_2O$ was used instead of plasmid DNA as a negative control.

Figure 5B:
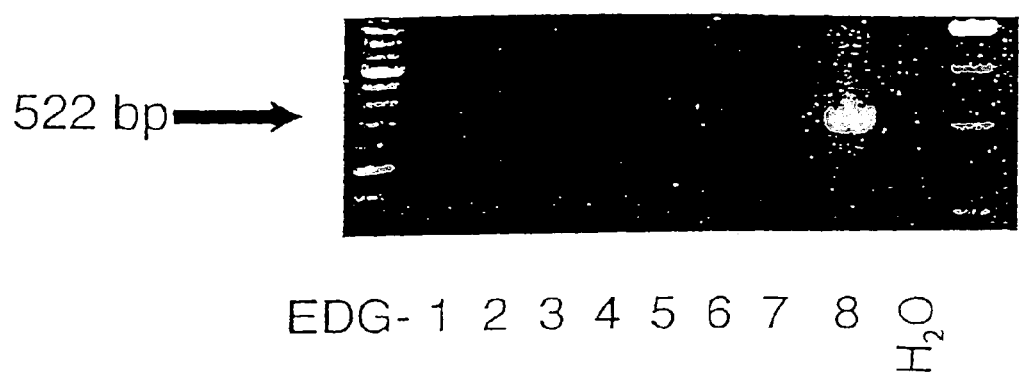

FIG. 5B: PCR analysis of EDG8 primers for specificity of amplification of EDG8 sequences. Primers, specific for the EDG8 sequence, were checked for potential amplification of the related EDG1–7 sequences, using the respective plasmids as templates. Agarose gel electrophoresis of the PCR products after 35 cycles of amplification with the GC-melt kit (as described in Experimental Procedures) is shown. The EDG8 specific 522 bp band occurred only when EDG8 was used as a template. $H_2O$ was used instead of plasmid DNA as a negative control.

FIG. 6: Experiments were performed according to example 3. Instead of lipids, a lipid library was used.

Figure 6A:
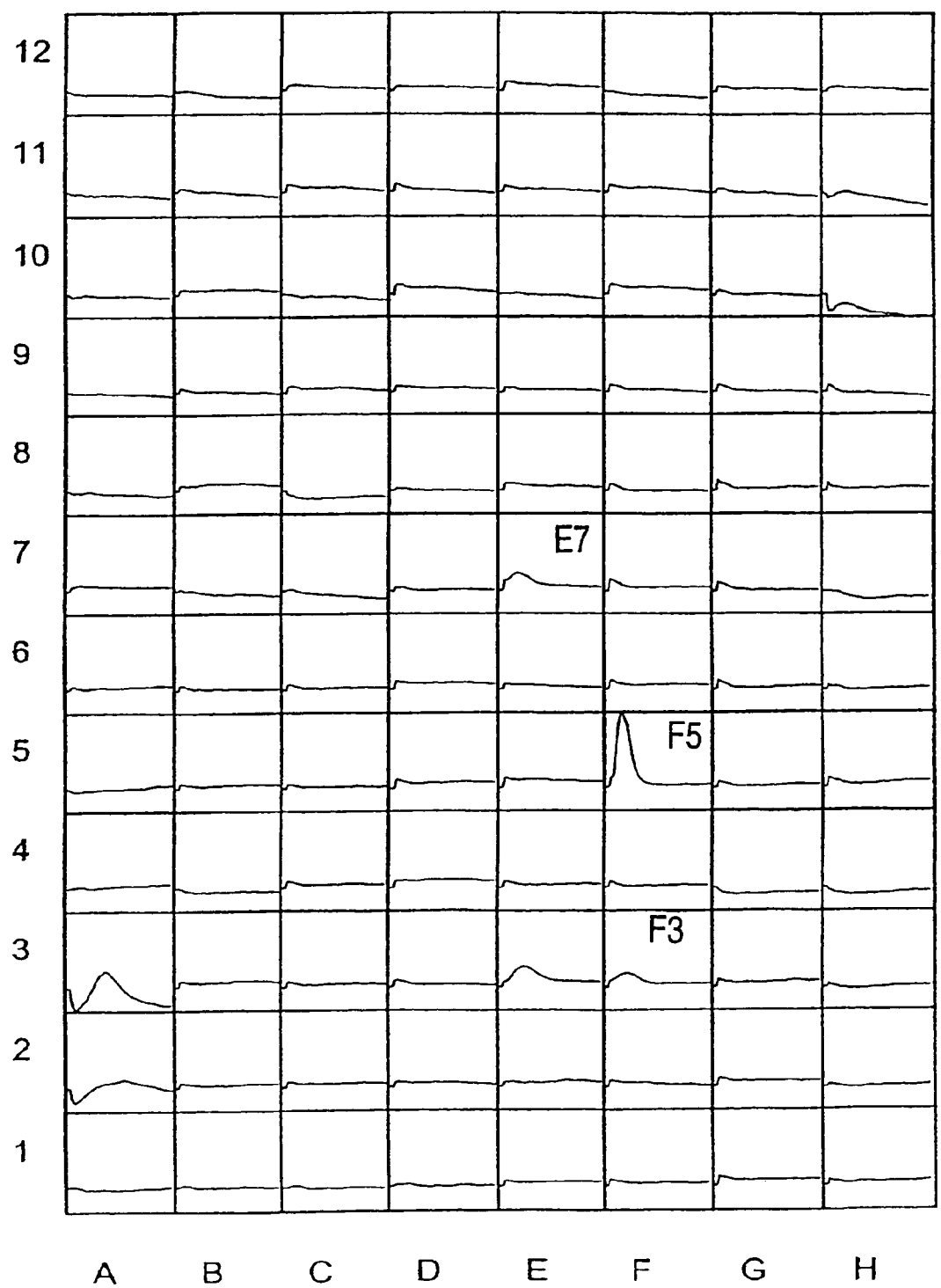

FIGS. 6A+B: Library plattes with rat EDG8 (r EDG8) and qi5.

Figure 6B:
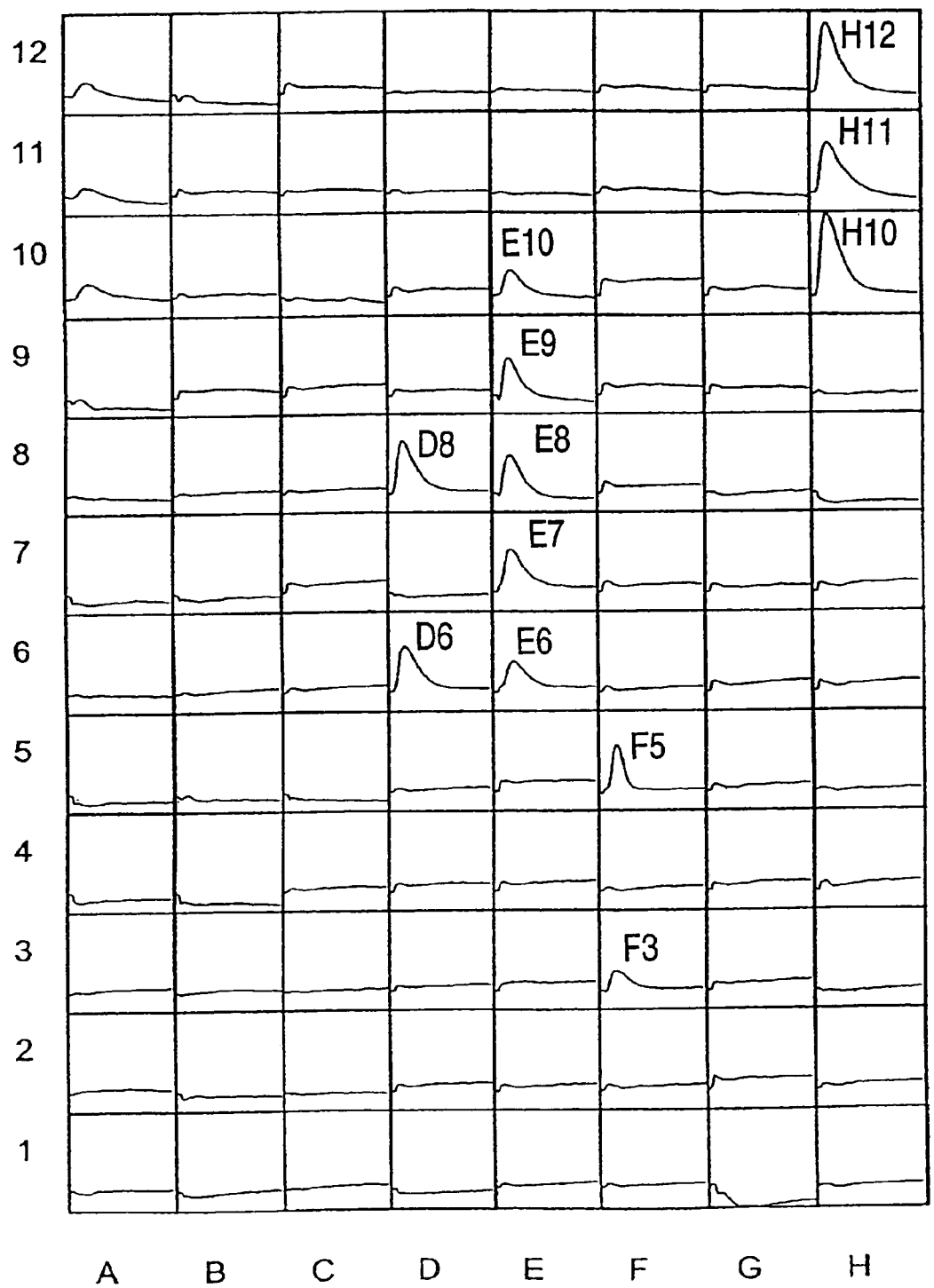

FIG. 6A: qi5 background.
FIG. 6B: Measurement with rEDG8.
FIG. 6C: Fluorescence change counts.
FIG. 7: Experiments were performed according to example 3. Instead of Lipids, a lipid library was used.

Figure 7A:
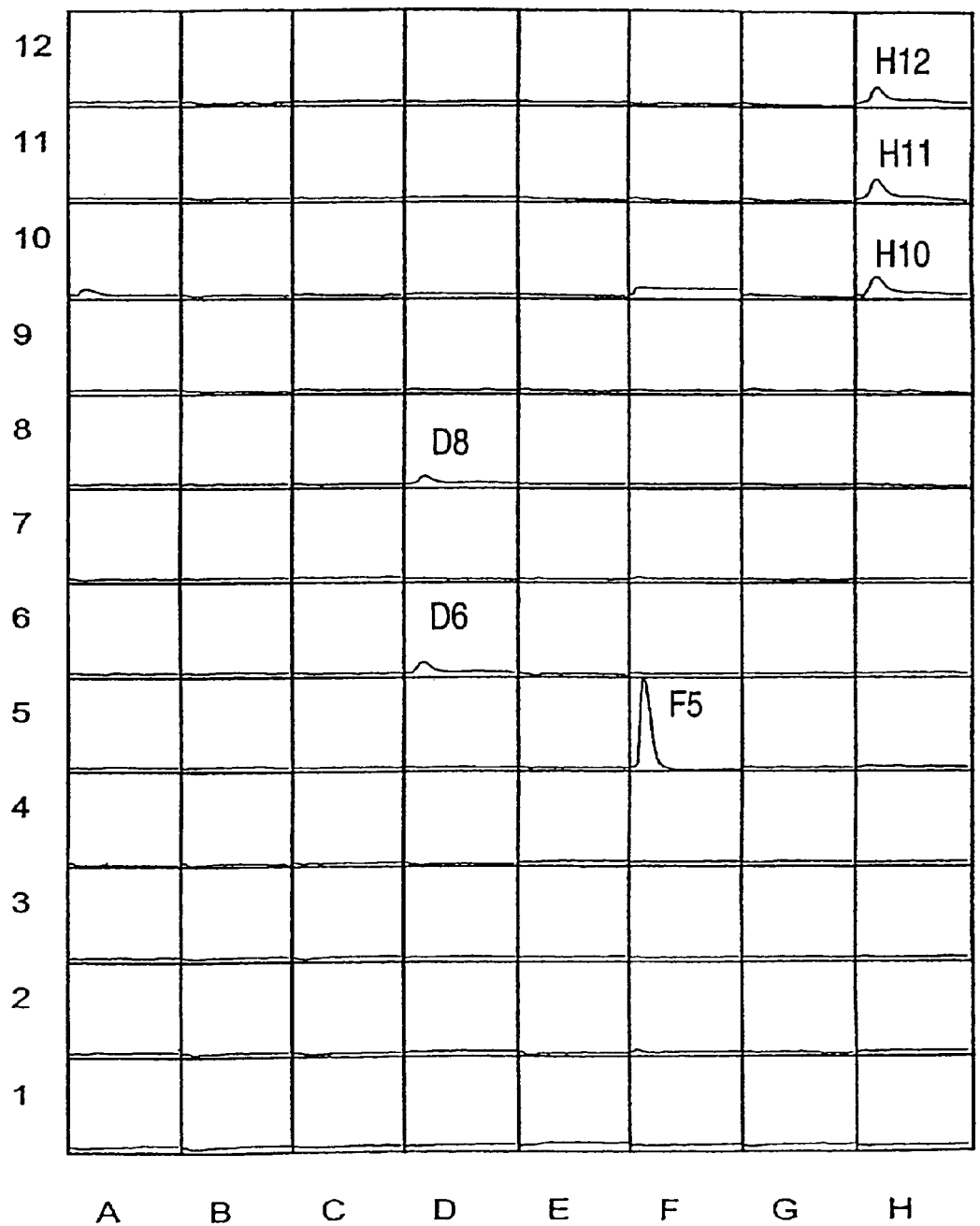

FIGS. 7A+B: Library plates with human EDG8 (hEDG8) and qi5.

Figure 7B:
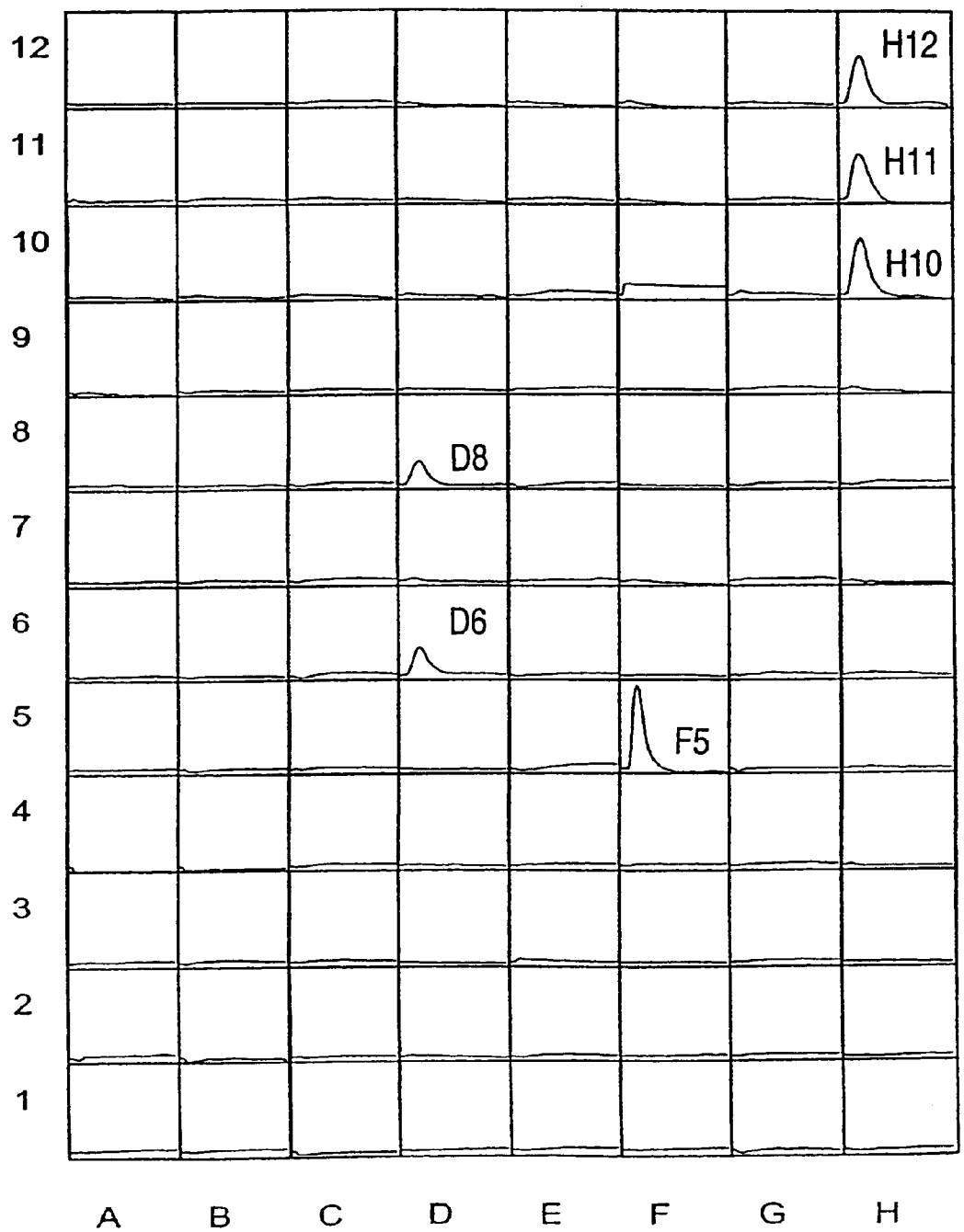
Figure 8:
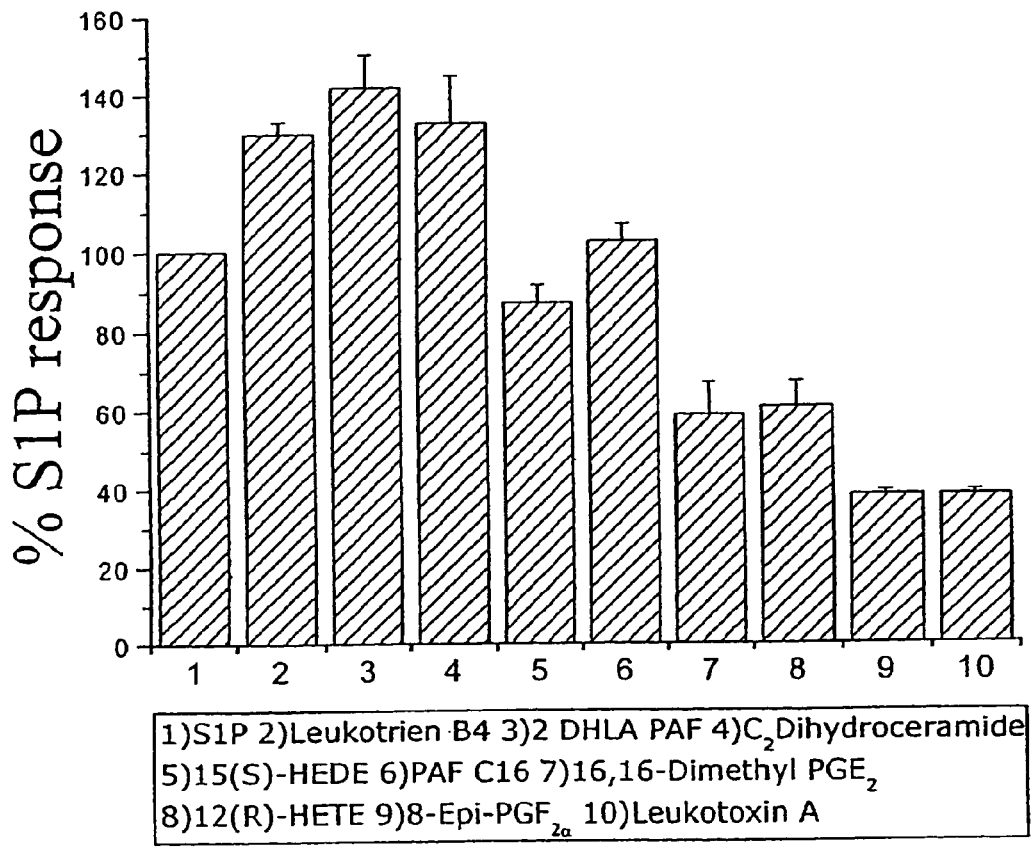
Figure 8:
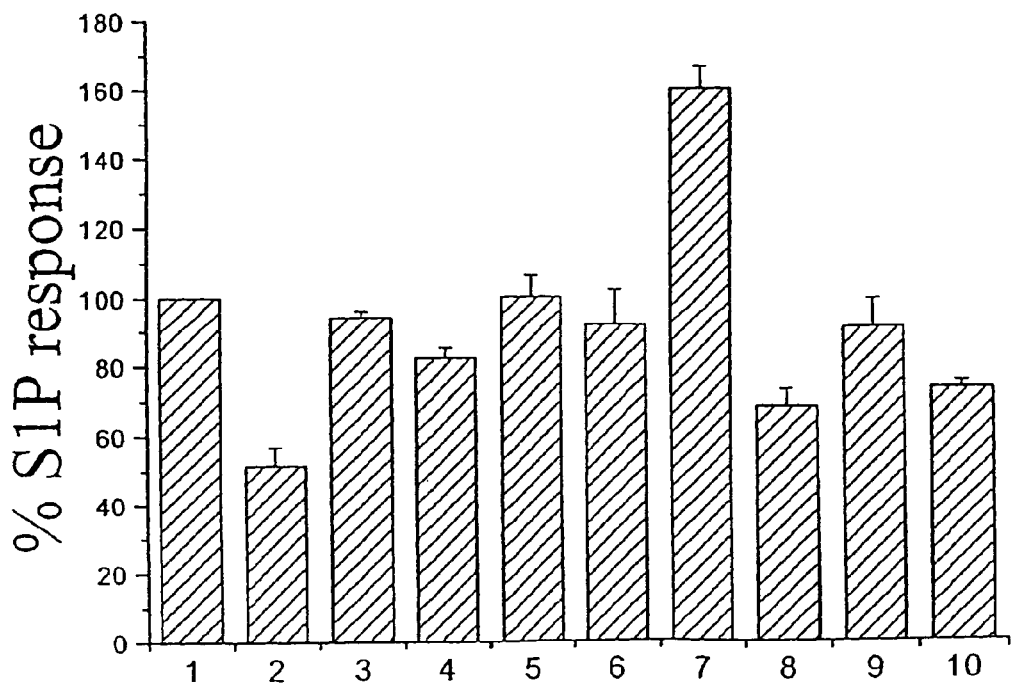
Figure 9A:
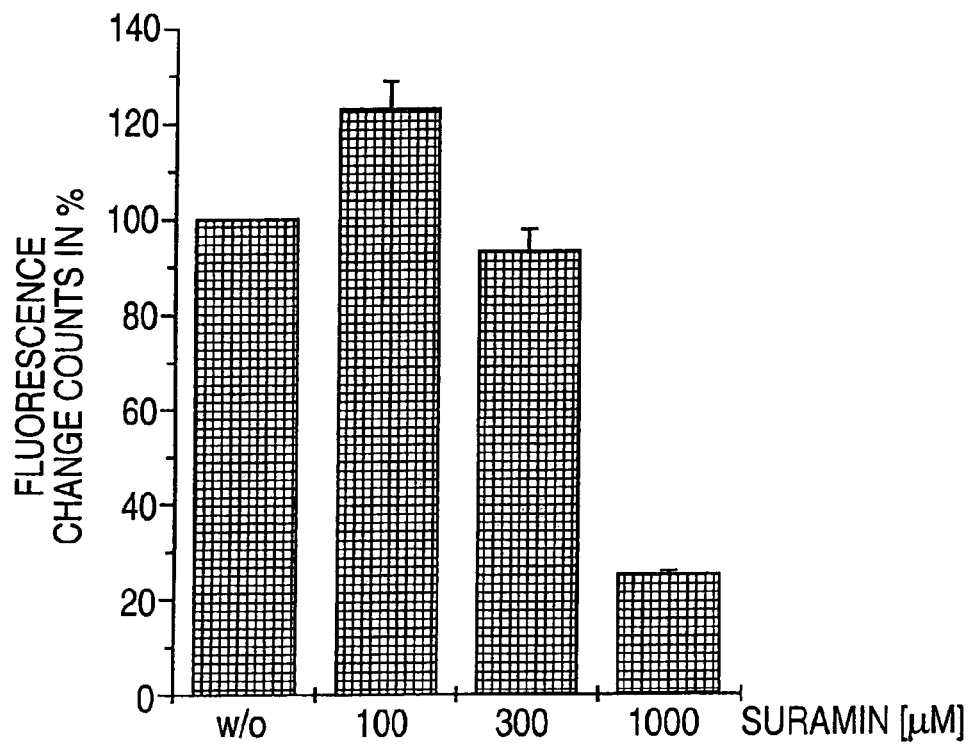
Figure 9A:
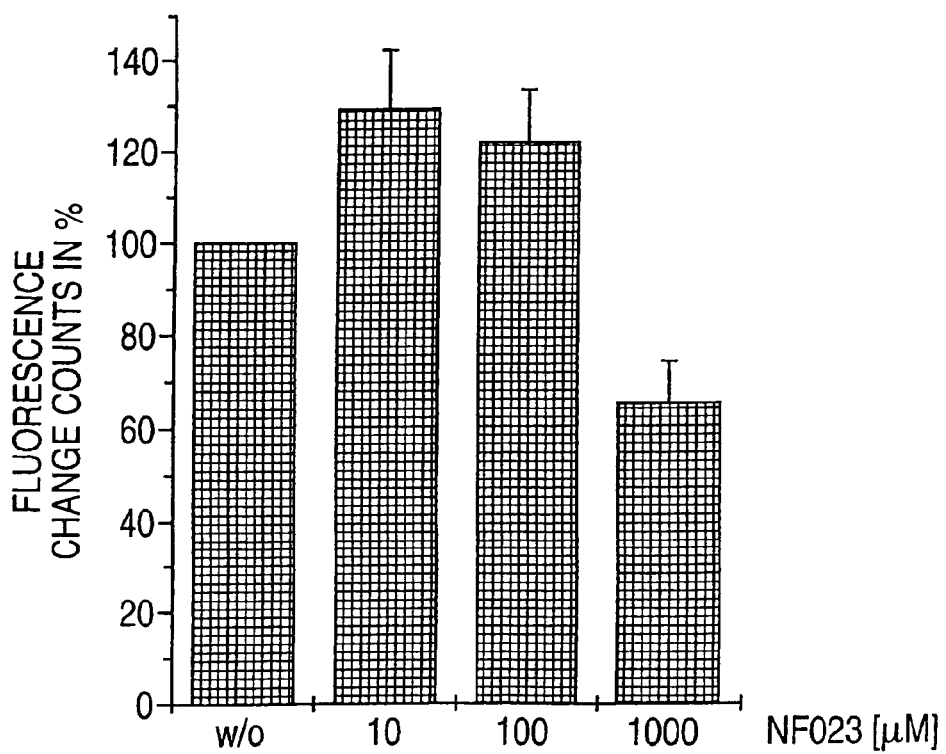
Figure 9B:
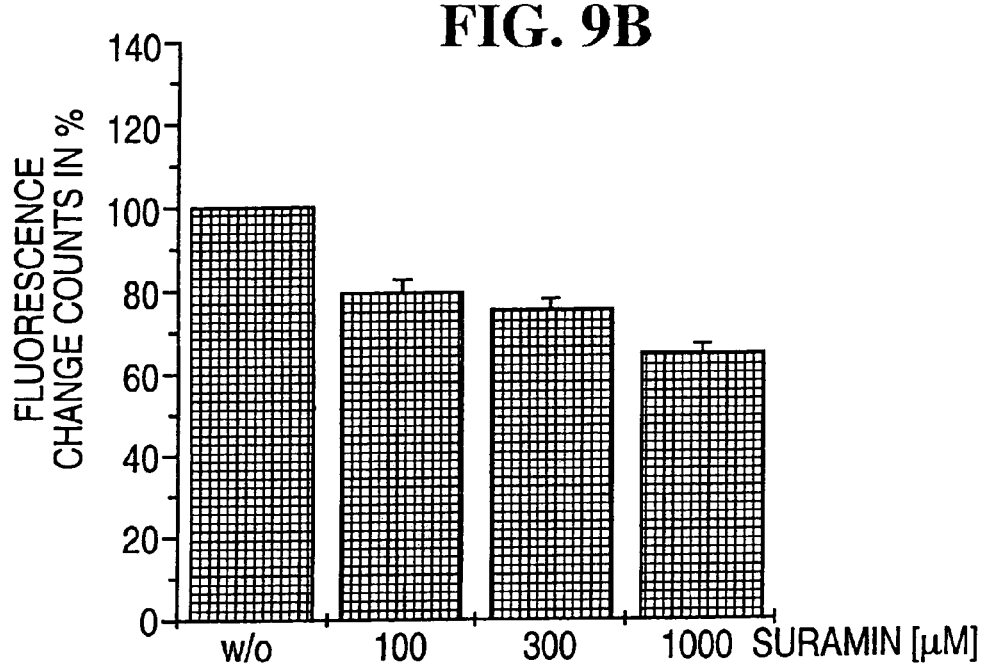
Figure 9B:
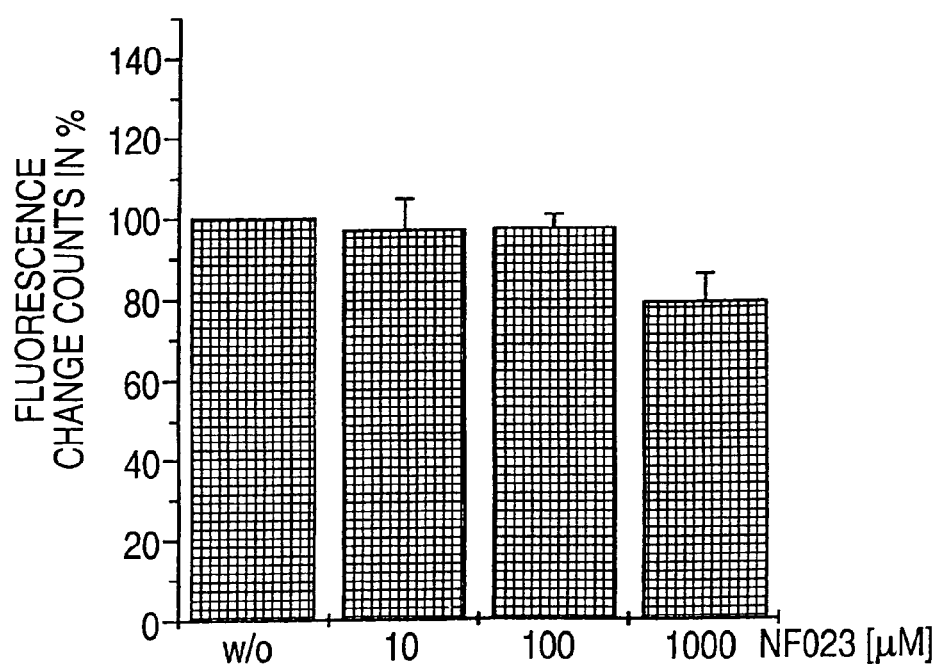

FIG. 7A: q15 background.
FIG. 7B: Measurement with hEDG8
FIG. 7C: Fluourescence change counts.
FIG. 8: Antagonism of S1P activation of rat and human EDG8. Transiently transfected CHO cells expressing rat EDG8 and $G\alpha_{qi5}$ (A) and HEK 293 cells expressing human EDG8 and $G\alpha_{qi5}$ (B) were incubated with test compounds, namely, 0.1 µM Leukotriene B4, 1 µM 2-DHLA-PAF (1-O-Hexadecyl-2-O-dihomo-γ-linolenoyl-sn-glycero-3-phosphorylcholine), 1 µM $C_2$ Dihydroceramide, 0.1 µM 15(S) HEDE (15(S)-Hydroxyeicosa-11Z,13E-dienoic acid), 1 µM PAF C16 (1-O-Hexadecyl-2-O-acetyl-sn-glycero-3-phosphorylcholine), 1 µM 16,16 Dimethyl $PGE_2$ (16,16-Dimethyl-Prostaglandin $E_2$) 12, 0.1 µM (R)-HETE (12(R)-Hydroxyeicosa-5Z,8Z,10E,14Z-tetraenioc acid), 1 µM 8-epi-$PGF_{2\alpha}$ (8epi-Prostaglandin $F_{2\alpha}$) 0.1 µM Leukotoxin A ((±) 9,10-EODE) or with solvent buffer for 3 min and then challenged with 1 µM S1P (sphingosine 1-phosphate). Peak fluorescence counts of cells preincubated with solvent buffer and then stimulated with 1 µM S1P were set 100%. Fluorescence change counts were recorded with the FLIPR as described in detail in Experimetal procedures. Data are means±SE of 2–3 independent experiments.

FIG. 9: Inhibition of S1P mediated intracellular calcium release by suramin and NF023 (8,8'-(carbonylbis(imino-3,1-phenylene))bis-(1,3,5-naphatlenetrisulfonic acid)) in cells transiently cotransfected with with human EDG8 and $G\alpha_{qi5}$ (A) and rat EDG8 and $G\alpha_{qi5}$ (B). Transfected cells were first treated with the indicated concentrations of the inhibitor or solvent buffer for 3 minutes (NF023 and suramin did not show any effect on $[Ca^{2+}]_i$ mobilization during the preincubation period). Cells were then stimulated with 1 µM S1P and in $[Ca^{2+}]_i$ measured with the FLIPR as described in the method section. Peak fluorescence counts were normalized and background responses of $G\alpha_{qi5}$-transfected cells were subtracted. S1P-mediated calcium release in the absence of inhibitor was set 100%. Data are means±SE of 4–7 independent experiments.

DETAILED DESCRIPTION OF THE INVENTION

The abbreviations used are:

S1P, sphingosine 1-phosphate; LPA, lysophosphatidic acid; dHS1P, dihydro sphingosine 1-phosphate; SPC, sphingosylphosphorylcholine; LPC, lysophosphatidylcholine; GPCR, G-protein-coupled receptor; G-protein, guanine nucleotide-binding protein; $[Ca^{2+}]_i$, intracellular Calcium concentration, RT-PCR, reverse transcription polymerase chain reaction; bp, base pair; ORF, open reading frame; EST, expressed sequence tag; FAF-BSA, fatty acid free bovine serum albumine; HUVECs, Human umbilical vein endothelial cells; HCAECs, human coronary artery endothelial cells; HMVEC-L, human microvascular endothelial cells from lung; HPAEC, human pulmonary artery endothelial cells.

In particular, the invention relates to an EDG8 polypeptide or a fragment thereof comprising an amino acid sequence which has at least about 90%, preferably at least about 95%, most preferred about 98% or more identity to the amino acid sequence SEQ ID NO. 2 or to a part of SEQ ID NO. 2. In particular the invention relates to an EDG8 polypeptide or a fragment thereof having amino acid sequence SEQ ID NO. 2 or a part thereof. In particular, the invention relates to an polypeptide encoded by SEQ ID NO. 1 or encoded by a polynucleotide that has at least about 90%, preferably at least about 95%, most preferred about 98% or more identity with SEQ ID NO. 1; preferably, such polypeptide has almost the same properties as human EDG 8; e.g. the same biological activity or functionality. One characteristic functionality of human EDG8 is that the polypeptide is a S1P receptor; it responds to S1P and optionally to related phospholipids like dHS1P or LPA as depicted and described in FIG. 2.

In an additional embodiment, a method of detecting a nucleic acid sequence encoding SEQ ID NO:1 in a biological sample comprising contacting a labeled nucleic acid probe that hybridizes with the nucleic acid sequence with the biological sample under conditions wherein the probe hybridizes with the nucleic acid sequence and detecting the hybridization of the probe to the nucleic acid sequence in the sample is provided.

By "biological sample" is meant any body fluid, tissue, cells or specimens obtained from a subject, such as from blood, urine, saliva, tissue biopsy and autopsy material. The genomic DNA from the biological samples may be used directly or may be amplified enzymatically by using PCR (Saiki et al., Nature 324:163–166, 1986) prior to analysis. RNA or cDNA may also be used for the same purpose. As an example, PCR primers complementary to the nucleic acid encoding the G-protein coupled receptor protein can be used as a probe to identify and analyze G-protein coupled receptors. The probe is labeled according to methods well-known to the skilled artisan, which are described below. Similarly, the detecting is conducted under hybridization conditions that are known to the skilled artisan and are describe further, below.

In an additional embodiment, the invention relates to a kit comprising one or more containers, wherein at least one container contains a detectably labeled antibody that selectively binds a polypeptide encoded by SEQ ID NO:1. A kit comprising one or more containers, wherein at least one container contains a detectably labeled nucleic acid probe that hybridizes under a stringency of 68° C. with a polynucleotide encoding SEQ ID NO:2 is also provided.

The invention further relates to a polypeptide consisting of the amino acid sequence of SEQ ID NO. 2.

This invention is further related to a DNA sequence wherein the DNA sequence has been selected from at least one of the following group of polynucleotide sequences:

a) a polynucleotide comprising the polynucleotide sequence of SEQ ID No 1, b) a polynucleotide which hybridizes under stringent hybridization conditions to a polynucleotide sequence according to a), c) a polynucleotide which hybridizes under low or medium stringency conditions to a polynucleotide sequence according to a), and d) a polynucleotide sequence complementary to a polynucleotide sequence as defined in one of a), b), or c).

Thus, in one embodiment, the invention relates to an isolated nucleic acid molecule encoding a EDG8 polypeptide comprising SEQ ID NO:2. In another embodiment, the invention relates to an isolated nucleic acid molecule comprising SEQ ID NO:1, a nucleic acid molecule that is at least 95% or about 95% dentical to SEQ ID NO:1, a nucleic acid molecule that hybridizes under stringent conditions to one of the above or is complementary to one of the above. In another embodiment, the nucleic acid sequence consists of SEQ ID NO. 1.

The nucleic acid molecule of the present invention may be in the form of RNA, such as mRNA, or in the form of DNA, including, for instance cDNA and genomic DNA obtained by cloning or produced synthetically. The DNA may be double-stranded or single-stranded. Single stranded DNA or RNA may be the coding strand, also known as the sense strand, or it may be the non-coding strand, also referred to as the anti-sense strand.

By "isolated" nucleic acid molecule is intended a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules further includes such molecules produced synthetically.

In another embodiment, the DNA sequence as mentioned above can be part of the genome of each organism which harbors a gene for EDG8. In particular, the DNA sequence is part of a mammal or a human being.

It is understood that all nucleic acid molecules encoding EDG8 are also included herein, as long as they encode a polypeptide having the biological activity of human EDG8. By "EDG8 biological activity" is meant that the molecule is a functional receptor for S1P, LPA, dHS1P and related lysophospholipid mediators. Such activity may be assayed using well known techniques in the art. One such assay employs assessment of the ability of $Ca^{2+}$ to mobilize as described in FIG. 2. Such nucleic acid molecules include naturally occurring, synthetic, and intentionally manipulated polynucleotides. For example, DNA encoding EDG8 may be subjected to site-directed mutagenesis. The nucleotide sequence for EDG8 also includes antisense sequences, and sequences encoding dominant negative forms of EDG8. The invention includes nucleotide sequences that are degenerate as a result of the genetic code. There are 20 natural amino acids, most of which are specified by more than one codon. Therefore, all degenerate nucleotide sequences are included in the invention as long as the amino acid sequence of EDG8 polypeptide encoded by the nucleotide sequence is functionally unchanged. When the sequence is RNA, the deoxynucleotides A, G, C, and T of SEQ ID NO:1 are replaced by ribonucleotides A, G, C, and U, respectively.

The present invention also includes fragments of the above described nucleic acid molecule. For instance, fragments include a segment of contiguous nucleotides of SEQ ID NO:1, which are at least about 10 bases, preferably about 15 bases or about 20 bases or 30 bases, or 40 bases, or 50 bases in length. Such fragments are useful as diagnostic probes and PCR primers, as set forth herein. Of course, larger fragments of the nucleic acid molecules of the present invention also are contemplated. Fragments or portions of the polynucleotides of the present invention also may be used to synthesize full-length polynucleotides of the present invention.

For example, a nucleic acid probe may be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The term "gene" means the segment of DNA involved in producing a polypeptide chain; it includes regions preceding and following the coding region (leader and trailer) as well as intervening sequences (introns) between individual coding segments (exons).

As described above, fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. In fact, probes of this type having at least up to 150 bases or greater may be preferably utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

Thus, the present invention is directed to polynucleotides having at least about a about 70% identity, preferably at least about 90% identity and more preferably at least about a 95% identity to a polynucleotide which encodes the polypeptide of SEQ ID NO:2, as well as fragments thereof, which fragments have at least 15 bases, preferably at least 30 bases, more preferably at least 50 bases and most preferably fragments having up to at least 150 bases or greater, which fragments are at least about 90% identical, preferably at least about 95% identical and most preferably at least about 97% identical to any portion of a polynucleotide of the present invention.

In another embodiment, the invention relates to a nucleic acid molecule that hybridizes under stringent condition to SEQ ID NO:1. By "stringent" conditions is meant washing of filters in 0.1×SSC, 0.1% SDS; 2 times for about 30 min. at about 68° C. (or about 5° C. below melting temperature). "Low medium" hybridization conditions means: washing of filters in 2×SSC, 0.1% SDS; 2 times for about 30 min. at about 68° C. (or about 10° C. below melting temperature).

The polynucleotides which hybridize to the above described polynucleotides in a preferred embodiment encode polypeptides which retain substantially the same biological function or activity as the mature polypeptide encoded by the cDNAs of SEQ ID NO:1. For example, such polypeptide could function as a receptor for S1P and related compounds, viz., LPA, dHS1P and related lysophospholipid mediators. Such activity may be assayed using well known techniques in the art. One such assay employs assessment of ability of $Ca^{2+}$ mobilization in response to S1P mediated by the receptor, e.g., EDG8 or a functional fragment thereof, in CHO cell as described in FIG. 2.

The nucleic acid molecule of the invention includes the DNA encoding SEQ ID NO:2 and conservative variations of SEQ ID NO:2. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The nucleic acid molecule of the present invention can be derived from any mammal, particularly humans. The preferred nucleic acid molecule is derived from humans. In the present invention, the nucleic acid molecule may be at least 95% or about 95% identical to SEQ ID NO:1. One of skill in the art can determine the percentage of sequence identity between two sequences by aligning the encoded amino acid sequences, determining the corresponding alignment of the encoding polynucleotides, and then counting the number of residues shared between the sequences being compared at each aligned position. No penalty is imposed for the presence of insertions or deletions, but insertion or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison reference sequence.

Percent identity is calculated for oligonucleotides of this length by not allowing gaps in either the oligonucleotide or the polypeptide for purposes of alignment. Whenever at least one of two sequences being compared is a degenerate oligonucleotide comprising an ambiguous residue, the two sequences are identical if at least one of the alternative forms of the degenerate oligonucleotide is identical to the sequence with which it is being compared. As an illustration, AYAAA is 100% identical to ATAAA, since AYAAA is a mixture of ATAAA and ACAAA. Methods to determine the homology and percent identity of sequences are well known in the art. These methods can be performed manually (using mathematical calculations) or with a computer program, such as the Wisconsin package version 10.1-Unix (Genetics Computer Group (GCG), Madison, Wis.).

Antibodies

In another embodiment of the invention, the EDG8 polypeptides of the invention, including fragments thereof, can be used to produce antibodies which are immunoreactive or bind to epitopes of the EDG8 polypeptides. Polyclonal antibodies and antibodies which consist essentially of pooled monoclonal antibodies with different epitopic specificities, as well as distinct monoclonal antibody preparations are encompassed by the invention.

The preparation of polyclonal antibodies is well-known to those skilled in the art. See, for example, Green et al., "Production of Polyclonal Antisera," in: Immunochemical Protocols pages 1–5, Manson, ed., Humana Press 1992; Coligan et al., "Production of Polyclonal Antisera in Rabbits, Rats, Mice and Hamsters," in: Current Protocols in Immunology, section 2.4.1, 1992, which are hereby incorporated by reference.

The preparation of monoclonal antibodies likewise is conventional. See, for example, Kohler & Milstein, Nature 256:495, 1975; Coligan et al., sections 2.5.1–2.6.7; and Harlow et al., in: Antibodies: a Laboratory Manual, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)," in: Methods in Molecular Biology, Vol. 10, pages 79–104, Humana Press, 1992.

Methods of in vitro and in vivo multiplication of monoclonal antibodies are well known to those skilled in the art. Multiplication in vitro may be carried out in suitable culture media is such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., Int. J. Cancer 46:310, 1990, which are hereby incorporated by reference.

Alternatively, a therapeutically useful anti-EDG8 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86:3833, 1989, which is hereby incorporated in its entirety by reference. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Nat'l Acad. Sci. USA 89:4285, 1992; Sandhu, Crit. Rev. Biotech. 12:437, 1992; and Singer et al., J. Immunol. 150:2844, 1993, which are hereby incorporated by reference.

Antibodies of the invention also may be derived from human antibody fragments isolated from a combinatorial immunoglobulin library. See, for example, Barbas et al., in: Methods: a Companion to Methods in Enzymology, Vol. 2, page 119, 1991; Winter et al., Ann. Rev. Immunol. 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13, 1994; Lonberg et al., Nature 368:856, 1994; and Taylor et al., Int. Immunol. 6:579, 1994, which are hereby incorporated by reference.

The term "antibody" includes intact molecules as well as fragments thereof, such as Fab, (Fab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; (Fab')$_2$, is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the EDG8 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), cmd tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Diagnostics

Further, the invention relates to a process for diagnosing a disease or a susceptibility to a disease (such as cancer, angiogenesis and inflammation that implicates S1P in pathophysiological states of the diseases) (Pyne and Pyne, Biochem J 349(Part 2):385, 2000) related to expression or biological activity of EDG8 polypeptide comprising:

a) determining the presence or absence of mutation in the nucleotide sequence encoding said EDG8 polypeptide in the genome of said subject; and/or b) analyzing for the presence or amount of the EDG8 polypeptide expression in a sample derived from said subject.

This invention is also related to the use of the nucleic acids encoding EDG8 as part of a diagnostic assay for detecting diseases or susceptibility to diseases related to the presence of mutated G-protein coupled receptor genes, such as EDG8 of SEQ ID NO:1. Such diseases are related to cell transformation, such as tumors and cancers.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 324:163, 1986) prior to analysis. RNA or cDNA may also be used for the same purpose. As an example, PCR primers complementary to the nucleic acid encoding the EDG8 polypeptide can be used to identify and analyze EDG8 mutations. For example, deletions and insertions can be detected by a change in size of the amplified product in comparison to the normal genotype. Point mutations can be identified by hybridizing amplified DNA to radiolabeled EDG8 receptor RNA or alternatively, radiolabeled EDG8 receptor antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242, 1985).

Sequence changes at specific locations may also be revealed by nuclease protection assays, such as RNase and S1 protection or the chemical cleavage method (e.g., Cotton et al., PNAS USA, 85:4397, 1985).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification (see Table-1). The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Expression Vector

The invention refers further to a vector, preferably a recombinant DNA expression vector. In one embodiment, the invention relates to a DNA vector comprising a nucleic acid molecule consisting of SEQ ID No. 1. The vector further comprises a polynucleotide element which renders the vector suitable for its multiplication in procaryotic or eucaryotic cells and a DNA sequence as aforementioned coding for the amino acid sequence or a polynucleotide sequence for EDG8. The term "expression vector" refers to a plasmid, virus or other vehicle known in the art that has been manipulated by insertion or incorporation of the EDG8 genetic sequences. This DNA element which renders the vector suitable for multiplication can be an origin of replication which works in procaryotic or eucaryotic cells. An example for an origin of replication which works in procaryotic cells is the colE1 ori. A recombinant vector needs further a selection marker for control of growth of these organisms which harbor the vector. Suitable selection markers include genes which protect organisms from antibiotics (antibioticum resistance) e.g. ampicillin, streptomycin, chloramphenicol or provide growth under compound deprived environmental conditions (auxotrophic growth conditions) when expressed as proteins in cells. In a preferred embodiment of the invention for multiplication of the said recombinant vector the procaryotic cells are bacteria. In special preferred versions of the inventions the bacteria are in particular bacteria of *Escherichia coli* or of *Bacillus* spec. In a further preferred embodiment of the invention for the multiplication of the said recombinant vector the eucaryotic cells are cells of a cell line or yeast cells. In special preferred versions of the invention the cells of the cell line are cells of a CHO cell line.

Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Thus, the nucleic acid sequence which encodes EDG8 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Thus, the said recombinant DNA of the present invention could provide for a promotor element which is operationally linked to a DNA sequence coding for the amino acid sequence or polynucleotide sequence of a EDG8 allowing transcription of the related RNA and/or expression of the related protein. Also included in the invention are those promoter elements which are sufficient to render promoter-dependent gene expression controllable for cell-type specific, tissue-specific, or inducible by external signals or agents; such elements may be located in the 5' or 3' regions of the gene. These promotor elements can be taken in preferred versions of the invention from procaryotic promoters or eucaryotic promoters. A procaryotic promoter is characterized by its ability to induce transcription in procaryotic organisms as a eucaryotic promoter is characterized by its ability to induce transcription in eucaryotic organisms. Both procaryotic and eucaryotic promoter elements can be preferred inducible promoters or further preferred constitutive promoters (see e.g., Bitter et al., Methods in Enzymology 153:516–544, 1987). An inducible promoter is switched on only when a signal event is present. The signal can be born by the organism's metabolism. Then it often consists of metabolic products, hormones, degradation products of macromolecules or other metabolic derived substances. The signal can also be provided by the environment. Then it may consist of radiation, temperature or chemical compounds of the environment. A constitutive promoter needs no induction for activity. When cloning in bacterial systems, inducible promoters such as pL of bacteriophage, gamma, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

The invention includes further a host cell and a cell culture comprised of said host cells. This host cell comprising at least one recombinant DNA vector as mentioned before. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art. When the host cell is taken from procaryotic cells it preferably consists of a cell of a bacterium in particular of *Escherichia coli* or *Bacillus* spec. When this host cell consists of a eucaryotic cell it is preferred a cell of a cell line in particular a cell of a CHO cell line.

This host cell can be produced by transforming the said host cell by a recombinant DNA vector comprising a DNA sequence coding for an amino acid sequence or polynucleotide sequence of a EDG8. The transformation can take place by routine methods used in microbiology as for example transformation of competent cells, $Ca^{2+}$-phosphate-precipitation or electroporation. By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding polypeptide of SEQ ID NO:1 or a fragment thereof. Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences of EDG8 of the invention. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Isolation and purification of microbial expressed polypeptide, or fragments thereof, provided by the invention, may be carried out by conventional means including preparative chromatography and immunological separations involving monoclonal or polyclonal antibodies.

The EDG8 expressed polypeptides can be recovered and purified from recombinant host cells and cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

In one embodiment, the invention provides substantially purified polypeptide of SEQ ID No:2 or a fragment thereof. Preferably, EDG8 translated polypeptide has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify EDG8-polypeptide using standard techniques for protein purification. The substantially pure polypeptide will yield a single major band on a non-reducing polyacrylamide gel. The purity of the polypeptide can also be determined by amino-terminal amino acid sequence analysis.

As explained above, the invention refers also to a protein encoded by one of the DNA sequences as aforementioned. This protein has activity of a EDG8. Activity of EDG8 is meant the molecule is a functional receptor for S1P, LPA, dHS1P and related lysophospholipid mediators. Such activity may be assayed using well known techniques in the art. One such assay employs assessment of ability of $Ca^{2+}$ mobilization as described in FIG. 2. As described above, further included is production of a protein wherein first a host cell harboring a recombinant vector including a DNA sequence encoding for an amino acid sequence or a polynucleotide sequence for EDG8 is propagated in a suitable growth medium chosen from either media for bacteria or eucaryotic cells depending on the related host cell type. These propagated cells are second harvested by common methods of biochemistry as centrifugation or filtration and processed to obtain crude cell extracts. These cell extracts third are purified subsequently by methods used for protein purification as size exchange chromatography, ion exchange chromatography, affinity chromatography and others to gain the protein of interest (EDG8 activity) separated from other compounds of the cell lysates.

The polypeptide of the invention may be expressed in a modified form, such as a fusion protein and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent storage and handling. Also, peptide moieties may be added to the polypeptide to improve purification. Such regions may be removed prior to final preparation of the peptide. Thus, in one embodiment, the invention relates to a fusion protein comprising a polypeptide consisting of the amino acid sequence of SEQ ID NO. 2. Additionally, the fusion protein of the invention could include amino acids of other members of the EDG family.

In one embodiment, the polypeptide of the present invention comprises the amino acid sequence of SEQ ID NO:2 and is encoded by the nucleotide sequence of SEQ ID NO:1. However, the polypeptide of the invention can be varied without significant effect on the structure or function of the molecule.

Minor modifications of the EDG8 primary nucleotide sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the EDG8 still exists.

The polypeptide of the present invention also includes fragments and variants of SEQ ID NO:2. "Variant" when referring to the polypeptide of SEQ ID NO:2, means polypeptides which retain essentially the same biological function or activity as a polypeptide comprising the full length SEQ ID NO:2.

A "fragment" is a segment of SEQ ID NO:2 that comprises contiguous amino acids.

The variant of the polypeptide SEQ ID NO:2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides. Such variants are deemed to be within the scope of those skilled in the art from the teachings herein.

The polypeptides of the present invention include the polypeptide of SEQ ID NO:2 as well as polypeptides which have at least about 70% similarity to the polypeptide of SEQ ID NO:2 and more preferably about at least a 90% similarity to the polypeptide of SEQ ID NO:2 and still more preferably at least about a 95% similarity to the polypeptide of SEQ ID NO:2 and also includes fragments of such polypeptides with such portion of the polypeptide generally containing about at least 8 consecutive amino acids and preferably about at least 30 to 50 consecutive amino acids.

As known in the art "similarity" between two polypeptides is determined by comparing the amino acid sequence and its conserved amino acid substitutes of one polypeptide to the sequence of a second polypeptide. This can be done manually (using mathematical calculations) or with a computer program, such as the Wisconsin package version 10.1-Unix (Genetics Computer Group (GCG), Madison, Wis.).

Fragments or portions of the polypeptides of the present invention may be employed for producing the corresponding full-length polypeptide by peptide synthesis, therefore, the fragments may be employed as intermediates for producing the full-length polypeptides. Fragments also may be used to generate antibodies, as described above.

In addition, the invention relates to a method for identifying compounds which bind to EDG8 polypeptide comprising:

a) contacting a cell comprising the expression system or a part of such a cell with a candidate compound; and
b) assessing the ability of said candidate compound to bind to said cells.

Preferably, the method for identifying compounds further includes determining whether the candidate compound effects a signal generated by activation of the EDG8 polypeptide at the surface of the cell, wherein a candidate compound which effects production of said signal is identified as an agonist.

In another embodiment of the invention, the method for identifying compounds further includes determining whether the candidate compound effects a signal generated by activation of the EDG8 polypeptide at the surface of the cell, wherein a candidate compound which effects production of said signal is identified as an antagonist.

Screening and Uses as Therapeutics

The present invention also relates to a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor. In the preferred embodiment, the receptor is EDG8.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, stroke, eating disorders, migraine headaches, cancer and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of G-protein coupled receptor antagonists include an antibody, or in some cases an oligonucleotide, which binds to the G-protein coupled receptor but does not elicit a second messenger response such that the activity of the G-protein coupled receptor is prevented. Antibodies include anti-idiotypic antibodies which recognize unique determinants generally associated with the antigen-binding site of an antibody. Potential antagonists also include proteins which are closely related to the ligand of the G-protein coupled receptor, i.e. a fragment of the ligand, which have lost biological function and when binding to the G-protein coupled receptor, elicit no response.

The invention also relates to an agonist or antagonist identified by such methods.

In another special embodiment of the invention, the method further includes contacting said cell with a known agonist for said EDG8 polypeptide; and determining whether the signal generated by said agonist is diminished in the presence of said candidate compound, wherein a candidate compound which effects a diminution in said signal is identified as an antagonist for said EDG8 polypeptide. The known agonist is for example S1P, LPA and/or dHS1P. The invention also relates to an antagonist identified by the method.

A compound can affect EDG8 by either stimulating or inhibiting EDG8 activity. An antagonist is a compound that directly or indirectly "inhibits" a signal generated by activation of the EDG8 polypeptide at the surface of the cell. An agonist is a compound that directly or indirectly "stimulates" a signal generated by activation of the EDG8 polypeptide.

Potential antagonists to the EDG8 polypeptides of the present invention include an antibody against the EDG8 polypeptides, or in some cases, an oligonucleotide, which bind to the EDG8 polypeptides and alter its conformation.

Potential antagonists also include antisense constructs produced by antisense technology. Antisense technology controls gene expression through triple-helix formation, etc. The number of EDG8 may be reduced through antisense technology, which controls gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073, 1979); Cooney et al, Science, 241:456, 1988); and Dervan et al., Science, 251: 1360, 1991), thereby preventing transcription and the production of the EDG8 polypeptides. The antisense RNA oligonucleotide hybridizes to the mRNA in vivo and blocks translation of the mRNA molecule into the EDG8 polypeptides (antisense—Okano, J. Neurochem., 56:560, 1991); Oligodeoxynucleotides as Antisense Inhibitors of Gene Expression, CRC Press, Boca Raton, Fla. 1988). The antisense constructs can be delivered to cells by procedures known in the art such that the antisense RNA or DNA may be expressed in vivo.

The antagonist or agonist compounds may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention in addition, relates to a method of preparing a pharmaceutical composition comprising:
  a) identifying a compound which is an agonist or an antagonist of EDG8,
  b) preparing the compound, and
  c) optionally mixing the compound with suitable additives.

The invention also relates to a pharmaceutical compound prepared by such a process.

The invention relates to a pharmaceutical, comprising as active ingredient for example such identified compound, an EDG8 polypeptide or a polynucleotide encoding for EDG8 or a part thereof.

In particular, the invention relates to a pharmaceutical, that can be used for the prevention and/or treatment of diseases associated with EDG8/S1P signal transduction, for example diseases associated with endothelial dysfunction such as for example Atheriosclerosis, Shoke, Hypertonie, coronary syndroms, cancer, thrombolylic diseases, affected wound healing and diseases accompanied by increased cell death. In another aspect of the invention, such pharmaceutical can be used for the prevention and/or treatment of diseases associated with a dysregulation of angiogenesis, such as for example tumor growth, rheumatical arthritis and diabetic setinopathy.

The study, reported about the cloning, chromosomal mapping, tissue expression and functional identification as a receptor for S1P of a novel GPCR, EDG8, the fifth functional receptor for sphingosine 1-phosphate.

In an effort to identify new G-protein coupled receptors of the EDG-family a database search with alignments of the currently known 18 members of this receptor family was performed, comprising human EDG1–7 sequences up to the putative EDGs from *Xenopus* and Zebra-fish. A multiple alignment of these sequences was created by CLUSTALW and used in a PSI-BLAST search to scan translated versions of human genomic DNA sequences, which were publicly available in the different EMBL sections. For translation of DNA into protein sequences, individual protein files within two respective STOP-codon were created and all proteins shorter than 50 amino acids were ignored. As the majority of GPCRs is unspliced searching for GPCRs within genomic sequences should bring about novel receptor proteins.

Figure 1C:
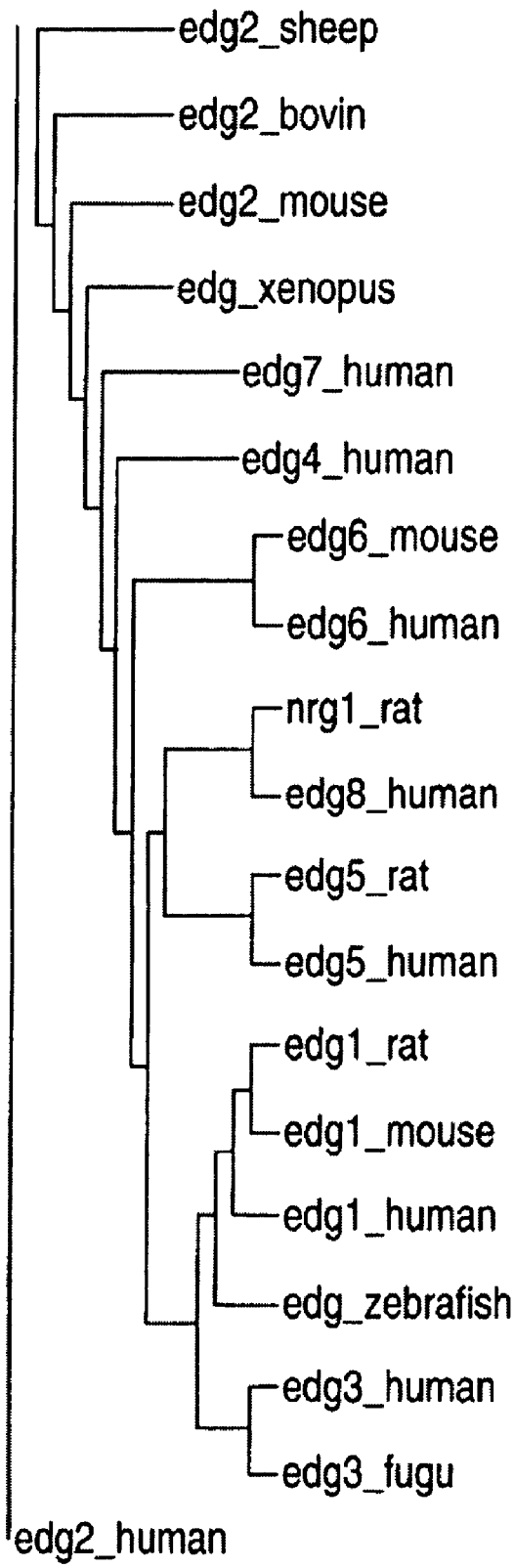
FIG. 1C: Phylogenetic tree of the EDG-family of receptors. The phylogenetic tree depicted was derived by the neighbor joining method performed with the GCG program Wisconsin package version 10.1-Unix (Genetic Computer Group (GCG), Madison, Wis.

Performing a PSI-BLAST search, the various cDNAs and genomic contigs, respectively, for the human EDG1–7 receptors were identified, and an additional genomic hit, highly homologous to human EDG5 (51% homology), termed EDG8. The nucleotide and amino acid sequence of the new putative GPCR are depicted in FIG. 1A and FIG. 1B. Hydropathy analysis (hydrophobicity plot not shown) suggests a seven transmembrane protein with three alternating extra- and intracellular loops, assumed to be the heptahelix structure common to GPCRs.

To shed more light on the relationships involved in the molecular evolution of the EDG-receptor family, a grow tree phylogram was constructed using the neighbor joining method (Genetic Computer Group (GCG), Madison, Wis. (FIG. 1C) Comparison of amino acid sequences). According to this phylogenetic tree, the human EDG-family can be divided into two distinct groups: EDG1, 3, 5 and 6 belonging to one, EDG2, 4 and 7 belonging to the other group. These two groups are discriminated further by their preference for different lipid ligands: EDB1, 3, 5, 6 are preferentially stimulated by sphingosine 1-phosphate (SI P) (Yatomi et al., J Biochem (Tokyo) 12:969, 1997; Lee et al., Science 279: 1552, 1998; Lee et al., J Biol Chem 273:22105, 1998; Ancellin and Hla, J Biol Chem 274:18997, 1999; Yamazaki et al., Biochem Biophys Res Commun 268:583, 2000; Van Brocklyn et al., Blood 95:2624, 2000), EDG2, 4 and 7 by lysophosphatidic acid (LPA) (Hecht et al., 1996; An et al., J Biol Chem 273:7906, 1998; Im et al., Mol Pharmacol 57:753, 2000). The newly identified EDG8 exhibited highest similarity (86.8% amino acid identity) to the rat nrg1-protein (FIG. 1C), a GPCR recently cloned by EST-expression profiling from a rat PC12 cell library (Glickman et al., Mol Cell Neuroscience 14:141, 1999), which probably represents the rat homologue of human EDG8. In the report of Glickman et al., however, the authors did not address the question of the activating ligand of this receptor. The high similarity between EDG8 and the known sphingosine 1-phosphate (SIP) receptors EDB1, 3 and 5 (48–51%) (FIGS. 1D and 1E) led to test the hypothesis that EDG8 may be a functional S1P-receptor.

In testing for S1P receptor activity, the EDG8 cDNA was introduced into chinese hamster ovary (CHO) cells by transient transfection. CHO cells were chosen as they exhibit minimal responses to sphingosin 1-phosphate in concentrations up to 1 µM but respond to S1P after transfection with the S1P preferring receptors EDG 1, 3 and 5 (Okamoto et al., J Biol Chem 273:27104, 1998; Kon et al., J Biol Chem 274:23940, 1999). To test functional receptor activity the mobilization of $[Ca^{2+}]_i$ was monitored for three reasons:

1) S1P has been reported to increase $Ca^{2+}$ in many cell types (Ghosh et al., 1990; Zang et al., 1991; Durieux et al., Am J Physiol 264:C1360, 1993; Chao et al., J Biol Chem 269:5849, 1994; Gosh et al., J Biol Chem 269:22628, 1994; Mattie et al., J Biol Chem 269:3181, 1994; Meyer zu Heringdorf et al., Naunyn-Schmiedeberg's Arch Pharmacol 354:397, 1997; Okajima et al., FEBS Lett 379:260, 1996; van Koppen et al., J Biol Chem 271:2082, 1996; Törnquist et al., Endocrinology 138:4049, 1997; Yatomi et al., J Biochem (Tokyo) 12:969, 1997; Noh et al., J Cell Physiol 176:412, 1998; An et al., Mol Pharmaco 55:787, 1999).

2) the identification of EDG1, 3, 5 and 6 as receptors for S1P has provided the molecular basis for a GPCR mediated mechanism and the receptors are known to mediate intracellular $Ca^{2+}$-release through either PTX-sensitive $G\alpha_i$ proteins or the PTX-insensitive $G\alpha_{q/11}$ pathway (Okamoto et al., J Biol Chem 273:27104, 1998; Kon et al., J Biol Chem 274:23940, 1999; Gonda et al., Biochem J 337:67, 1999).

3) all currently known S1P-responding EDG-receptors (except EDG6) are present in endothelial cells (A. Niedernberg et al., submitted), in which intracellular $Ca^{2+}$ release is a major pathway in the generation of NO, an important factor in vascular biology. Thus, identification of the complete set of S1P receptors, involved in intracellular $Ca^{2+}$ mobilization could help clarify the role of the individual subtypes in endothelial cell signaling.

Figure 2B:
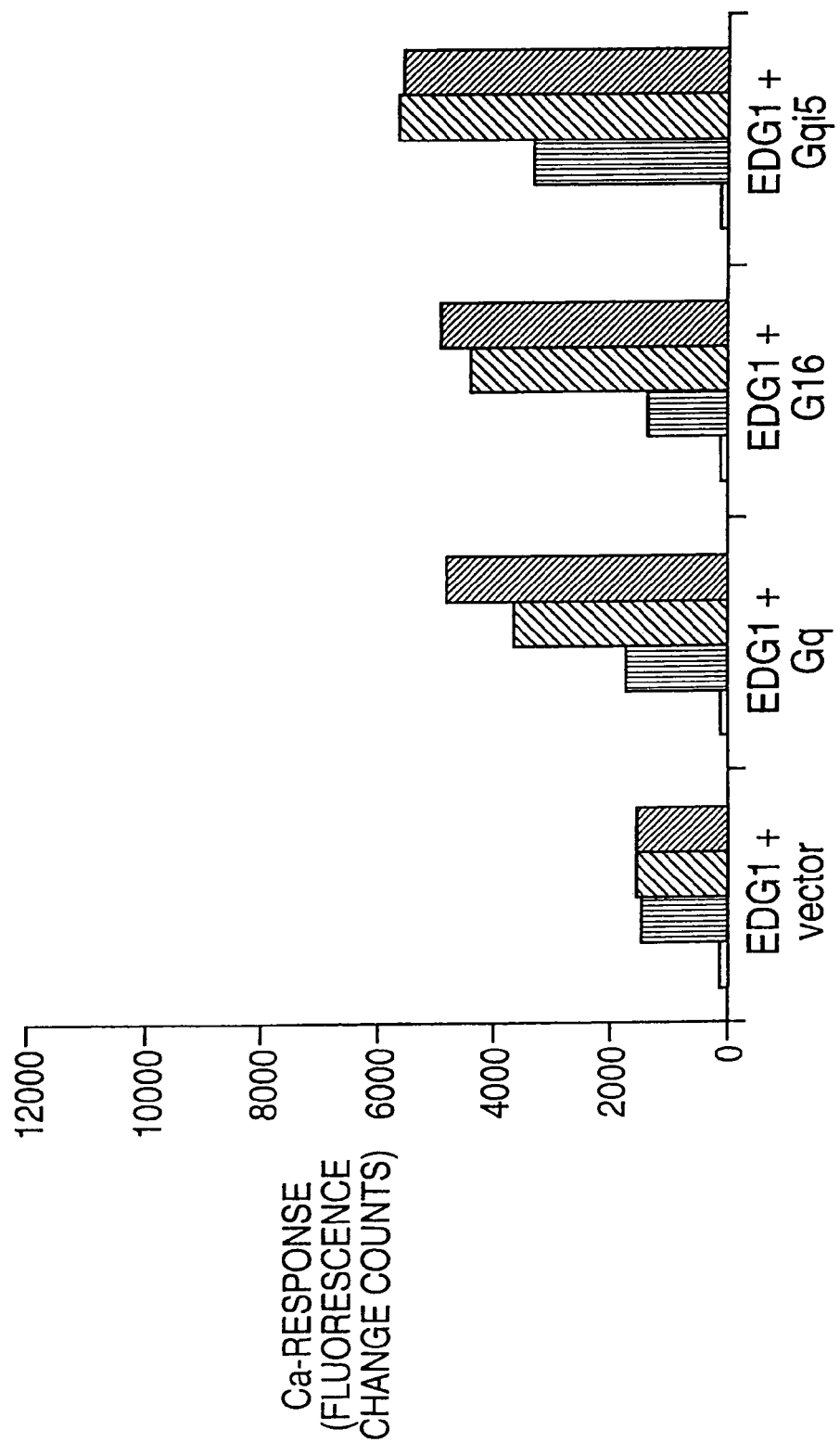

FIG. 2 depicts measurement of the intracellular $Ca^{2+}$ concentration, mediated by S1P via the putative S1P receptor EDG8. For sake of comparison, the S1P-receptors EDG1, 3, 5, and 6, which have been reported to mobilize $[Ca^{2+}]_i$, were included. $[Ca^{2+}]_i$ were recorded as real time measurements using the Fluorescence plate imaging reader (FLIPR, Molecular Devices). Initially, CHO cells transfected with empty vector DNA were stimulated with different concentrations of S1P (10, 100, 1000 nM). None of the applied S1P concentrations was capable of eliciting significant rises in intracellular $Ca^{2+}$ (FIG. 2A), suggesting that S1P receptors are not expressed in CHO cells or, if expressed, are unable to signal via the endogeneous $G\alpha_q$ pathway. To address this issue, the G protein chimera $G\alpha_{qi5}$, which confers onto Gi coupled receptors the ability to stimulate the Gq pathway, and $G\alpha_{16}$, which links Gi- and Gs coupled receptors to PLCβ and subsequent intracellular $Ca^{2+}$-mobilization were used. Upon stimulation with S1P, $G_{qi5}$- and $G_{16}$-transfected CHO cells did not give rise to significant increases in $[Ca^{2+}]_i$ (FIG. 2A). However, transient transfection of CHO-cells with the cDNAs coding for the EDG1, 3 and 5 receptor conferred S1P-responsiveness to the cells: it was confirmed that EDG1, 3 and 5 mobilize $[Ca^{2+}]_i$ in response to S1P (FIGS. 2B, C, D) (Kon et al., J Biol Chem 274:23940, 1999). As already known for a large number of Gq-coupled receptors, coexpression of $G\alpha_q$ augments the EDG1 and 5-mediated $Ca^{2+}$-response as compared with the $Ca^{2+}$ signal induced by stimulation of endogeneous $G\alpha_q$. In case of EDG3, additional exogeneously added $G\alpha_q$ did not further improve the signal intensity. These results are in agreement with the findings reported by Kon et al. (J Biol Chem 274:23940, 1999), who showed that the EDG3-subtype causes the most robust enhancement of intracellular $Ca^{2+}$.

In case of EDG6, Yamazaki et al. (Biochem Biophys Res Commun 268:583, 2000) obtained an S1P-induced mobilization of $[Ca^{2+}]_i$ but in this study, investigators failed to detect a significant $Ca^{2+}$ increase above basal levels in the absence of any cotransfected G-protein α subunit (FIG. 2E). The reason for this discrepancy could be the cellular background (CHO cells in this study vs. K562 cells in Yamazaki et al., Biochem Biophys Res Commun 268:583, 2000), as they reported a pertussis toxin (PTX)-sensitive $Ca^{2+}$-responses, indicating the involvement of Gi-type G-proteins. In this case the $Ca^{2+}$ signal would be elicited by βγ, released from activated $G\alpha_i\beta\gamma$ heterotrimers. The $G\alpha_i$-induced $Ca^{2+}$ signals are known to be much smaller in intensity as compared with the $Ca^{2+}$ signals induced by bona-fide Gq-linked receptors (Kostenis et al., J Biol Chem 272:19107, 1997). It may be that detection of such $[Ca^{2+}]_i$ concentrations is beyond the sensitivity of the FLIPR system.

EDG8 did not release $[Ca^{2+}]_i$ when stimulated with S1P (10, 100, and 1000 nM) (FIG. 2F), but gained the ability to mobilize $Ca^{2+}$ upon cotransfection with $G\alpha_{16}$, a G-protein α subunit, known to couple GPCRs from different functional classes to the Gq-PLCβ pathway or $G\alpha_{qi5}$, a mutant G-protein a subunit that confers onto Gi-linked receptors the ability to stimulate Gq (Conklin et al., 1993). These results show that EDG8 is a functional receptor for S1P and that EDG8-induced $Ca^{2+}$ responses are due to a non-Gq pathway, probably the activation of phospholipase Cβ2 by βγ subunits of the Gi proteins. Furthermore, these results provide additional evidence that the S1P-preferring EDG-receptors couple differentially to the Gq and Gi pathways: EDG3 ist the most potent $Ca^{2+}$-mobilizing receptor and overexpression of $G\alpha_q$ does not further improve $Ca^{2+}$ signalling; EDG1 and 5 induce moderate $Ca^{2+}$-increases, that can be significantly improved by cotransfection of $G\alpha_q$ or a chimeric $G\alpha_{qi5}$ protein; EDG8-mediated $Ca^{2+}$-responses require cotransfection of $G\alpha_{qi5}$ or $G\alpha_{16}$.

To check whether the EDG8 receptor also reacts to related lysophospholipid mediators, the inventors examined the abilities of lysophosphatidic acid (LPA), dihydrosphingosin 1-phosphate (dHS1P), sphingosylphosphorylcholine (SPC) and lysophosphatidylcholine (LPC) to increase intracellular $Ca^{2+}$ in CHO cells transiently transfected with the EDG8 receptor and the G-protein α subunits $G\alpha_{16}$ and $G\alpha_{qi5}$ (FIG. 3). Besides S1P, which was the most potent activator of EDG8, LPA and dHS1P evoked $[Ca^{2+}]_i$ increases in concentrations of 100 and 1000 nM. SPC and LPC, respectively, failed to generate any significant response in concentrations up to 1 μM. These data show that EDG8 is a S1P preferring receptor, but also responds to related phospholipids like dHS1P or LPA, as has also been reported for EDG1, which is a high affinity receptor for S1P and a low affinity receptor for LPA (Lee et al., J Biol Chem 273:22105, 1998). Therefore, EDG8 receptor has the characteristic functionality to respond to S1P and related phospholipids like DMS 1P or LPA. The response to S1P and other related phospholipides can for example be determined as described in Example 3. Cells containing the respective Gα can be obtained as described in Example 2.

Next, the expression pattern of the EDG8 gene in human tissues was investigated by Northern blot analysis (FIG. 4). Tissues positive for EDG8 RNA were skeletal muscle, heart and kidney, lower abundance of RNA was seen in liver and placenta, no signal was detected in brain, thymus, spleen, lung and peripheral blood leukocytes. In all tissues a single RNA transcript of 5.5 kb was observed after hybridization with a DIG-labelled EDG8 antisense RNA probe. EDG8 exhibits highest similarity to the rat nrg1-GPCR (Glickman et al., Mol Cell Neuroscience 14:141, 1999) with an amino acid identity of 86.8% (FIG. 1C) suggesting that it may be the human homolog of the rat nrg1 protein. However, the expression pattern of human EDG8 is quite different from the rat nrg1-receptor, which is found almost exclusively in brain (Glickman et al., Mol Cell Neuroscience 14:141, 1999). This finding suggests that EDG8 may represent a closely related but entirely different receptor from nrg1, rather than the human homolog. Never the less, it does not rule out the possibility that EDG8 and nrg1 are homologs with entirely different, species-dependent expression patterns.

As the first member of the EDG-family of GPCRs—EDG1—was originally cloned as an endothelial differentiation gene from phorbol-myristic-acetate-treated differentiating human endothelial cells (Hla and Maciag, J Biol Chem 265:9308, 1990) and subsequently cloned from a human umbilical vein endothelial cell library exposed to fluid shear stress as an upregulated gene it is reasonable to assume that EDG receptors play an important role in the regulation of endothelial function. Therefore, the presence of EDG8 transcripts in several human endothelial cell lines was analyzed.

RT-PCR analysis of human umbilical vein endothelial cells (HUVECs), human coronary artery endothelial cells (HCAECs), human microvascular endothelial cells of the lung (HMVEC-L) and human pulmonary artery endothelial cells (HPAEC) revealed EDG8 expression in all cell lines tested (FIG. 5A). In FIG. 5B it is shown that EDG8 specific primers indeed solely amplify EDG8 sequences and none of the related EDG1–7 sequences. These findings suggest that the presence of EDG8 in different peripheral organs may be due to its localization in endothelial cells; it does not rule out, however, that EDG8 transcripts occur in cell types other than endothelial cells.

The expression of EDG8 in addition to EDG1, 3, and 5 (Rizza et al., Laboratory Investigation 79:1227, 1999) in HUVECs and several other endothelial cell lines is intriguing in view of all the reports regarding S1P effects on endothelial cell signalling. Hisano et al. (Blood 93:4293, 1999) reported that S1P protects HUVECs from apoptosis induced by withdrawal of growth factors and stimulates HUVEC DNA synthesis; the authors derived a model for cell-cell interactions between endothelial cells and platelets but the S1P-receptor responsible for HUVEC-protection of apoptosis could not be identified. Rizza et al. (Laboratory Investigation 79:1227, 1999) reported that S1P plays a role in endothelial cell leukocyte interaction in that S1P induces expression of cell adhesion molecules in human aortic endothelial cells, allowing monocytes and neutrophils to attach. These effects were blocked by pertussis toxin, suggesting the involvement of a Gi-coupled S1P receptor. The responsible S1P-receptor subtype, however, could not be identified and the EDG8 receptor was not included at the time of this study. Expression profiling of all EDG receptors in individual cell lines and the use of EDG receptor subtype selective compounds will clearly be necessary to help determine the role of the individual S1P receptors in endothelial cell signalling mechanisms.

Finally, the mapping of EDG receptors in genomic sequences allowed to derive the chromosomal localization for four genes of this family (Table 1). Interestingly, so far, four EDG-receptors including EDG8 are located on chromosome 19. In addition, the genomic sequence allowed the determination of the structure of the genes: the S1P-preferring receptors EDG1, 3, 5 and 8 are intronless as opposed to the LPA-preferring subtypes 2, 4 and 7, that contain an intron in the open reading frame in TMVI. These data suggest that in addition to the activating ligand and the degree of homology, the two subclasses of lysophospholipid receptors can be discriminated further by their genomic structure. The genomic structure of new potential EDG/LPA-receptor family members may also help predict the nature of the activating lipid ligand.

In conclusion, a new member of the EDG-family of G-protein coupled receptor, human EDG8, was isolated. This receptor functions as a cellular receptor for sphingosine 1-phosphate. EDG8 could exclusively be detected in peripheral tissues like skeletal muscle, heart and kidney and several human endothelial cell lines. It is conceivable that the expression in endothelial cells may account for the broad tissue distribution of this receptor. The existence of at least eight EDG-receptors for lysophospholipids suggests that receptor subtype selective agonists and antagonists will essentially be necessary for a better understanding of the biology of lysophospholipids and their respective receptors.

TABLE 1: Chromosomal localization, gene structure and accession number of the respective EDG genomic clones. Mapping of EDG receptors in genomic sequences allowed to derive a chromosomal assignment for EDG1, 2, 4–8. The chromosomal localization of EDG3 was obtained from Yamaguchi et al. (1996). Genomic sequences also revealed EDG1, 3, 5, 6 and 8 to be unspliced as opposed to EDG2, 4 and 7, which contain an intron in their open reading frame (ORF).

| EDG | Chromosomal localization | spliced/unspliced in ORF | according BAC accession number: |
|---|---|---|---|
| EDG1 | 1p21.1–21.3 | unspliced | AL161741 |
| EDG2 | 9q31.1–32/ /18p11.3 | spliced | AL157881/ /AP000882 |
| EDG3 | 9q22.1–q22.2 | unspliced | |
| EDG4 | 19p12 | spliced | NT_000939 |
| EDG5 | 19 | unspliced | AC011511 |
| EDG6 | 19p13.3 | unspliced | AC011547 |
| EDG7 | 1p22.3–31.2 | spliced | AL139822 |
| EDG8 | 19 | unspliced | AC011461 |

EXAMPLE 1

Molecular Cloning of the Human EDG8 Receptor

As the putative human EDG8 sequence is intronless, the receptor was cloned from human genomic DNA (CLONTECH, Palo Alto, Calif., 94303-4230) via polymerase chain reaction (PCR). PCR conditions, established to amplify the EDG8 sequence were 94° C., 1 min followed by 35 cycles of 94° C., 30 sec, 68° C., 3 min, using GC-Melt Kit (CLONTECH, Palo Alto, Calif.). Primers designed to amplify the EDG8 sequence contained a HindIII site in the forward, and a EcoRI site in the reverse primer, respectively. The 1197 bp PCR product was cloned into the pCDNA3.1 (+) mammalian expression vector (Invitrogen, Carlsbad, Calif.) and sequenced in both directions.

EXAMPLE 2

Cell Culture and Transfection

CHO-K1 cells were grown in basal ISCOVE medium supplemented with 10% fetal bovine serum at 37° C. in a humidified 5% $CO_2$ incubator. For transfections, $2 \times 10^5$ cells were seeded into 35-mm dishes. About 24 hr later cells were transiently transfected at 50–80% confluency with the indicated receptor and G-protein constructs (1 μg of plasmid DNA each) using the Lipofectamine transfection reagent and the supplied protocol (GIBCO). 18–24 hr after transfection cells were seeded into 96well plates at a density of 50,000 cells per well and cultured for 18–24 additional hr until used in the functional FLIPR assays.

The cDNA for Gα16 was cloned from TF1 cells by RT-PCR and ligated into the pCDNA1.1 mammalian expression vector (Invitrogen). Murine wild type Gαq was cloned from cells by RT-PCR and inserted into the BamHI-NsiI-sites of pCDNA1.1. To create the C-terminally modified $G\alpha_{qi5}$ subunit, in which the last five aa of wt Gαq were replaced with the correspoding $G\alpha_i$ sequence, a 175-bp BglII-NsiI fragment was replaced, in a two piece ligation, with a synthetic DNA fragment, containing the desired codon changes. The correctness of all PCR-derived sequences was verified by sequencing in both directions.

EXAMPLE 3

Fluorometric Imaging Plate Reader (FLIPR) Assay

Twenty-four hours after transfection, cells were splitted into 96-well, black-wall microplates (Corning) at a density of 50,000 cells per well. 18–24 hr later, cells were loaded with 95 µl of HBSS containing 20 mM Hepes, 2.5 mM probenecid, 4 µM fluorescent calcium indicator dye Fluo4 (Molecular Probes) and 1% fetal bovine serum for 1 h (37° C., 5% $CO_2$). Cells were washed three times with HBSS containing 20 mM Hepes and 2.5 mM probenecid in a cell washer. After the final wash, the solution was aspirated to a residual volume of 100 µl per 96 well. Lipid ligands were dissolved in DMSO as 2 mM stock solutions (treated with ultrasound when necessary) and diluted at least 1:100 into HBSS containing 20 mM HEPES, 2.5 mM probenecid and 0.4 mg/ml fatty acid free bovine serum albumine. Lipids were aliquoted as 2× solutions into a 96 well plate prior to the assay. The fluorometric imaging plate reader (FLIPR, Molecular Devices) was programmed to transfer 100 µl from each well of the ligand microplate to each well of the cellplate and to record fluorescence during 3 min in 1 second intervals during the first minute and 3 second intervals during the last two minutes. Total fluorescence counts from the 18-s to 37-s time points are used to determine agonist activity. The instrument software normalizes the fluorescent reading to give equivalent initial readings at time zero.

EXAMPLE 4

Northern Blot Analysis

Human multiple tissue Northern blots were purchased from CLONTECH (Palo Alto, Calif., 94303-4230, USA). Antisense RNA probes were generated by subcloning nucleotides 279–1197 of the coding region into the Bam HI-Eco RI sites of the expression vector PSPT18 (Roche Diagnostics, Mannheim, Germany) and subsequent random priming with a DIG-RNA Labeling kit (Roche Diagnostics, Mannheim, Germany), using T7 RNA polymerase. Hybridization was carried out at 68° C. for 16 h in hybridization buffer (Dig Easy Hyb Roche Diagnostics, Mannheim, Germany). Each blot was washed, blocked and detected as indicated in the standard protocol with the DIG Wash and Block Buffer set (Roche Diagnostics, Mannheim, Germany) and treated with 1 ml CSPD ready-to-use (Roche Diagnostics, Mannheim, Germany) for 15 min, 37° C. and developed for 5 min on the Lumiimager (Roche). Finally, each blot was stripped (50% formamide, 5% SDS, 50 mM Tris/HCl pH 7,5; 80° C., 2×1 hour) and rehybridized with a GAPDH anti-sense RNA probe as an internal standard.

EXAMPLE 5

RNA Extraction and RT-PCR

RNA was prepared from different endothelial cell lines (HUVECS, HCAEC, HMVEC-L, HPAEC) using the TRIzol reagent (Hersteller, Lok.). Briefly, for each endothelial cell line, cells of a subconfluent 25 cm2 tissue culture flask were collected in 2,5 ml TRIzol and total RNAs were extracted according to the supplied protocol. The purity of the RNA preparation was checked by veryfying the absence of genomic DNA. An aliquot of RNA, corresponding to ~5 µg, was used for the cDNA generation using MMLV reverse transcriptase and the RT-PCR kit from STRATAGENE. RT-PCR was carried out in a volume of 50 µl, the RT-PCR conditions were set to 65° C. for 5 min, 15 min at RT, 1 hour at 37° C., 5 min at 90° C., chill on ice.

The cDNA templates for the PCR reactions (35 cycles of 94° C. for 30 sec, 68° C. for 3 min) were the reverse transcribed products of RNAs isolated from human endothelial cell lines (HUVECS,HCAEC, HMVEC-L, HPAEC). Typically, 1–5 µl of reverse transcribed cDNAs were used as templates for the PCR reactions.

EXAMPLE 6

Sources of Materials 1-oleoyl-LPA, sphingosin 1-phosphate (S1P), dihydrosphingosin 1-phosphate (dHS1P), lysophosphatidylcholine (LPC), sphingosylphosphorylcholine (SPC) and fatty acid free BSA were from SIGMA (P.O. Box 14508, St. Louis, Mo. 63178). CHO-K1 cells were obtained from the American Type culture collection (ATCC, Manassas, Va.), cell culture media and sera from GIBCO BRL (Gaithersburg, Md.), the Ca fluorescent dye FLUO4 and pluronic acid from Molecular devices (Sunnyvale Calif. 94089-1136, USA) human northern blot membrane from CLONTECH (1020 East Meadow Circle, Palo Alto, Calif. 94303-4230, USA.), commercially available cDNAs (heart, fetal heart, left atrium, left ventricle, kidney, brain, liver, lung, aorta) from Invitrogen, oligonucleotides from MWG-Biotech AG (Ebersberg, Germany), the RT-PCR kit from SIGMA, the GC-melt PCR kit from Clontech (Palo Alto, Calif.), the expression plasmid pcDNA3.1 for EDG8 and pCDNA1.1 for expression of G-protein α subunits from Invitrogen (Carlsbad, Calif. 92008), competent DH5α from GIBCO and MC 1063 from Invitrogen.

All citations, including patents, patent applications, journal articles, books and other publications are herein incorporated by reference in their entirety.

What is claimed is:

1. A method for identifying a compound that binds to a polypeptide comprising the amino acid sequence of SEQ ID NO:2, the method comprising the steps of:
    a) contacting a host cell with a candidate compound, wherein the host cell comprises an expression vector which comprises a polynucleotide encoding a polypeptide comprising the amino acid sequence of SEQ ID NO:2, said polynucleotide being operationally linked to a promoter, wherein the polynucleotide is selected from the group consisting of:
        (i) a polynucleotide encoding SEQ ID NO:2, and
        (ii) a polynucleotide of SEQ ID NO:1, and
    b) assessing the ability of said candidate compound to bind to said polypeptide of said host cell.

2. The method of claim 1 further comprising determining whether the said candidate compound effects a signal generated by activation of said polypeptide at the surface of the cell, wherein said candidate compound which effects production of said signal is identified as an agonist.

3. The method of claim 1 further comprising determining whether said candidate compound effects a signal generated by activation of said polypeptide at the surface of the cell, wherein the said candidate compound which effects production of said signal is identified as an antagonist.

4. The method of claim 1 further comprising contacting said cell with a known agonist for said polypeptide; and determining whether the signal generated by said agonist is diminished in the presence of said candidate compound, wherein the said candidate compound which effects a diminution in said signal is identified as an antagonist for said polypeptide.

5. The method of claim 4, wherein the said known agonist is selected from the group consisting of S1P, LPA and dHS1P.

6. A method of preparing a pharmaceutical composition comprising:
    a) identifying by the method of claim 2, 3 or 4 an agonist or antagonist of a protein comprising the amino acid sequence of SEQ ID NO:2;
    b) preparing the compound; and
    c) mixing the compound with a pharmaceutically acceptable carrier.

* * * * *